US012595505B2

(12) United States Patent　　　(10) Patent No.:　US 12,595,505 B2
Fisher et al.　　　　　　　　　　　(45) Date of Patent:　Apr. 7, 2026

(54) COMPOSITIONS AND METHODS FOR CELLULAR PHENOTYPE ASSESSMENT OF A SAMPLE USING CONFINED VOLUME ARRAYS

(71) Applicant: PATTERN BIOSCIENCE, INC., Austin, TX (US)

(72) Inventors: Matthew Fisher, Austin, TX (US); Nicolas Arab, Austin, TX (US); Ross Johnson, Austin, TX (US); David Bussian, Austin, TX (US)

(73) Assignee: PATTERN BIOSCIENCE, INC., Austin, TX (US)

( * ) Notice: Subject to any disclaimer, the term of this patent is extended or adjusted under 35 U.S.C. 154(b) by 717 days.

(21) Appl. No.: 17/251,706

(22) PCT Filed: Jun. 13, 2019

(86) PCT No.: PCT/US2019/036899
§ 371 (c)(1),
(2) Date: Dec. 11, 2020

(87) PCT Pub. No.: WO2019/241471
PCT Pub. Date: Dec. 19, 2019

(65) Prior Publication Data

US 2021/0151132 A1　　May 20, 2021

Related U.S. Application Data

(60) Provisional application No. 62/747,309, filed on Oct. 18, 2018, provisional application No. 62/684,736, filed on Jun. 13, 2018.

(51) Int. Cl.
*C12Q 1/24*　　　(2006.01)
*G01N 21/64*　　　(2006.01)
(Continued)

(52) U.S. Cl.
CPC ........... *C12Q 1/24* (2013.01); *G01N 21/6408* (2013.01); *G01N 21/6428* (2013.01);
(Continued)

(58) Field of Classification Search
USPC .......................................................... 702/19
See application file for complete search history.

(56) References Cited

U.S. PATENT DOCUMENTS 6,673,578 B1　　1/2004　Uemori et al.
6,990,290 B2　　1/2006　Kylberg et al.
(Continued)

FOREIGN PATENT DOCUMENTS

CN　　　103224880　　　7/2013
JP　　　2004505233　　　2/2004
(Continued)

OTHER PUBLICATIONS

Adan, Aysun, et al. "Flow cytometry: basic principles and applications." Critical reviews in biotechnology 37.2 (2017): 163-176. (Year: 2017).*
(Continued)

*Primary Examiner* — Karlheinz R. Skowronek
*Assistant Examiner* — Mary C Leverett
(74) *Attorney, Agent, or Firm* — Norton Rose Fulbright US LLP

(57) ABSTRACT

Certain embodiments of the invention are directed to evaluating and identifying cells by recording and interpreting a time-dependent signal produced by unique cell respiration and permeability attributes of isolated viable cells. Some methods comprise dividing the sample into two or more sub-samples or sample portions, mixing each sub-sample or sample portion with one or more reagents and/or one or more reactants forming distinct sub-sample or sample portion mixtures, compartmentalizing each of the sub-sample or (Continued)

sample portion mixtures into a plurality of small volume compartments, monitoring characteristics of the small volume compartments over time and collecting compartment data, and transmitting the collected data to at least one neural network.

19 Claims, 21 Drawing Sheets

(51) Int. Cl.

| | | |
|---|---|---|
| *G06V 10/764* | (2022.01) | |
| *G16B 40/20* | (2019.01) | |
| *G16B 40/30* | (2019.01) | |
| *G16C 20/70* | (2019.01) | |
| *G16H 10/40* | (2018.01) | |
| *G16H 20/10* | (2018.01) | |
| *G16H 50/20* | (2018.01) | |

(52) U.S. Cl.
CPC ........... *G06V 10/764* (2022.01); *G16B 40/20* (2019.02); *G16B 40/30* (2019.02); *G16C 20/70* (2019.02); *G16H 10/40* (2018.01); *G16H 20/10* (2018.01); *G16H 50/20* (2018.01)

(56) References Cited

U.S. PATENT DOCUMENTS

| | | | |
|---|---|---|---|
| 9,739,783 B1 | 8/2017 | Kumar et al. | |
| 9,934,364 B1 * | 4/2018 | Kumar ................... | G06N 3/045 |
| 2005/0084923 A1 | 4/2005 | Mueller et al. | |
| 2010/0227767 A1 | 9/2010 | Boedicker et al. | |
| 2018/0106786 A1 | 4/2018 | Arab et al. | |
| 2018/0247195 A1 | 8/2018 | Kumar et al. | |
| 2019/0218497 A1 | 7/2019 | Boedicker et al. | |

FOREIGN PATENT DOCUMENTS

| | | |
|---|---|---|
| JP | 2012531890 | 12/2012 |
| JP | 2018500926 | 1/2018 |
| WO | WO 2003/025113 | 3/2003 |
| WO | WO 2011/001138 | 1/2011 |
| WO | WO 2017/027380 | 2/2017 |
| WO | WO 2017/218202 | 12/2017 |
| WO | WO 2018/069866 | 4/2018 |

OTHER PUBLICATIONS

Mazutis, Linas, et al. "Single-cell analysis and sorting using droplet-based microfluidics." Nature protocols 8.5 (2013): 870-891. (Year: 2013).*

Broeren, M. A. C., et al. "Antimicrobial susceptibility testing in 90 min by bacterial cell count monitoring." Clinical Microbiology and Infection 19.3 (2013): 286-291. (Year: 2013).*
U.S. Appl. No. 60/962,426, filed Jul. 26, 2007, Boedicker, et al.
U.S. Appl. No. 61/052,490, filed May 12, 2008, Boedicker, et al.
Dangla, et al., "Droplet Microfluidics Driven By Gradients of Confinement," *PNAS*, 110(3): 853-858, 2013.
International Preliminary Report on Patentability Issued in Corresponding PCT Patent Application No. PCT/US2019/036899, dated Dec. 15, 2020.
International Search Report and Written Opinion Issued in Corresponding PCT Patent Application No. PCT/US2019/036899, dated Aug. 29, 2019.
Mezgec & Seljak, et al., "NutriNet: A Deep Learning Food and Drink Image Recognition System for Dietary Assessment," Nutrients, 9(7), e657: 1-9, 2017.
Pofahl, et al., "Use of an Artificial Neural Network to Predict the Length of Stay in Acute Pancreatitis," Am Sur, 64(9): 868-872, 1998.
Yu, et al., "Phenotypic Antimicrobial Susceptibility Testing with Deep Learning Video Microscopy," Anal Chem, 90(10): 6314-6322, 2018.
Jiang et al., "High-Throughput Single-Cell Cultivation on Microfluidic Streak Plates" *Appl Environ Microbiol.* 2016, 82, pp. 2210-2218.
Liu, Ronghui. *Big Data Architecture Technology and Case Analysis.* the first version, Northeast Normal University Press, 2018, pp. 155-157 (No English translation provided; in accordance with MPEP § 609.04(a).III, the required concise explanation of the relevance of this document can be found in the English translation of the Office Action issued in corresponding Chinese Application No. 201980053262.5, dated Jan. 4, 2024 (Ref. Des. C3) in which this document was cited).
Office Action issued in corresponding Chinese Application No. 201980053262.5, dated Jan. 4, 2024 (English translation provided).
Office Action issued in corresponding Japanese Application No. 2021-518861, dated Mar. 4, 2024 (English translation provided).
Extended European Search Report issued in corresponding European Application No. 19818870.8, dated Feb. 15, 2022.
Office Action issued in correspondence Japanese Application No. 2021-518861, dated Jun. 26, 2023 (English Translation provided).
Office Action issued in corresponding Indian Application No. 202037055281, dated Sep. 29, 2022.
Iino et al., "Design of a large-scale femtoliter droplet array for single-cell analysis of drug-tolerant and drug-resistant bacteria" *Frontiers in Microbiology* 2013, 4(300), 6 pages.
Office Action issued in corresponding European Application No. 19818870.8, dated Mar. 10, 2025.
Office Action issued in corresponding Japanese Application No. 2021-518861, dated Dec. 12, 2024 (English Translation provided).

* cited by examiner

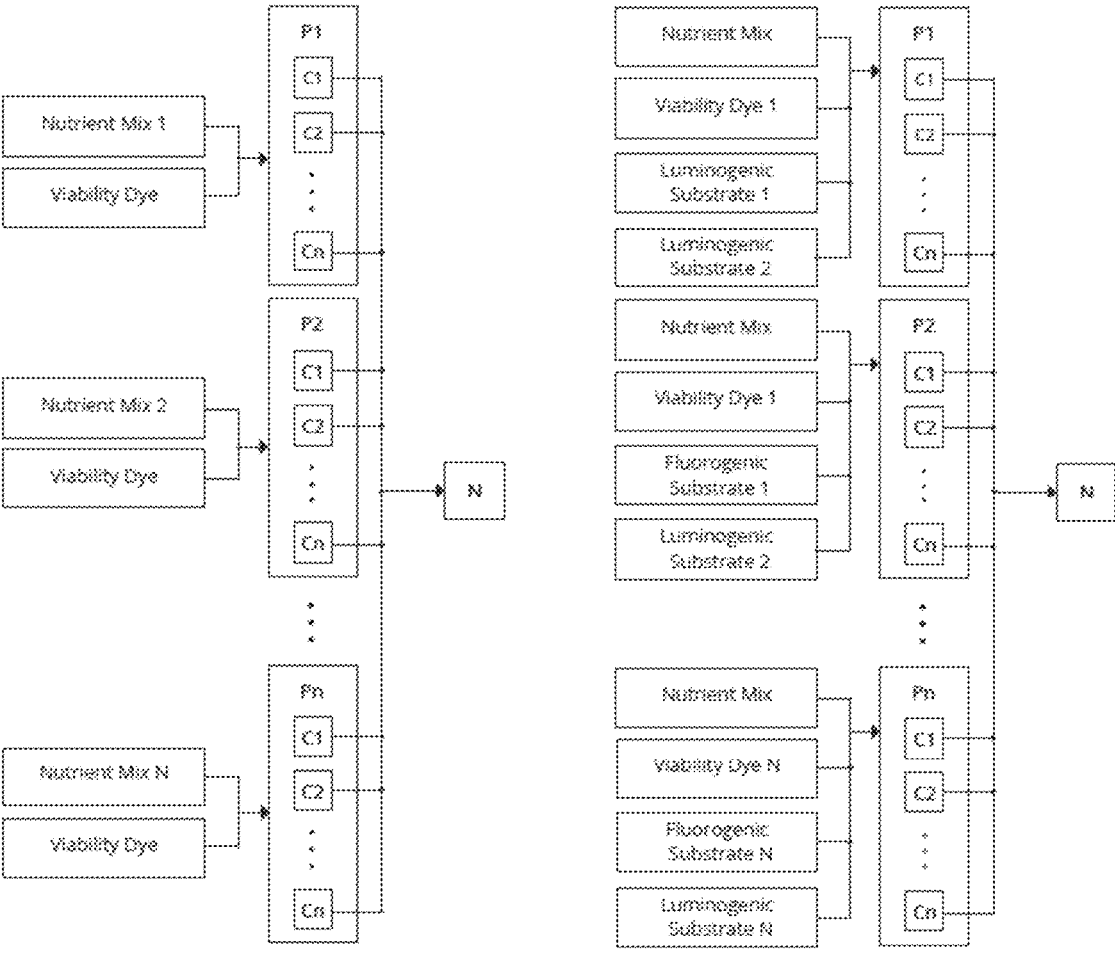
FIG. 8A                              FIG. 8B

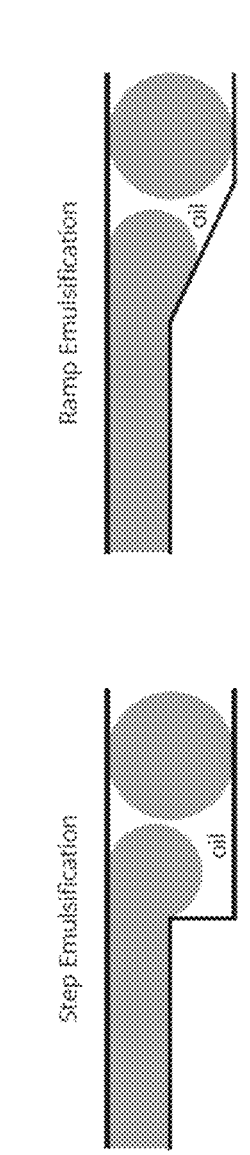
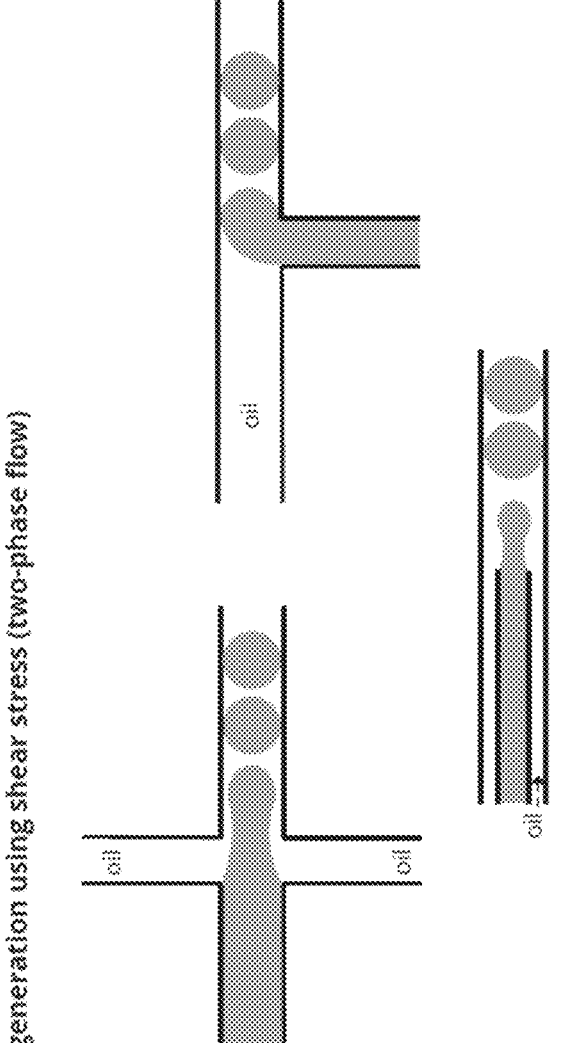
FIG. 15

Isolated bacterium

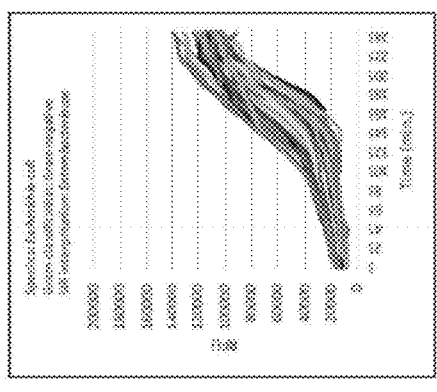
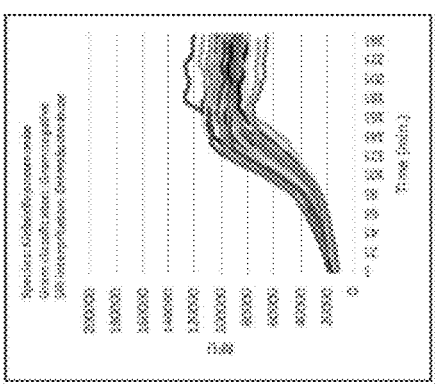
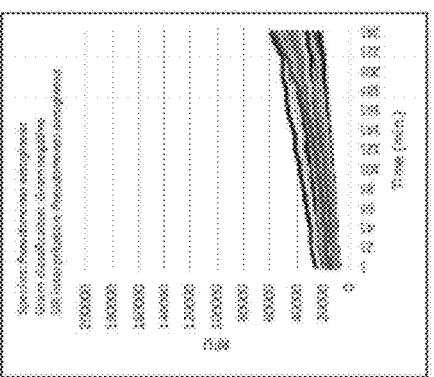
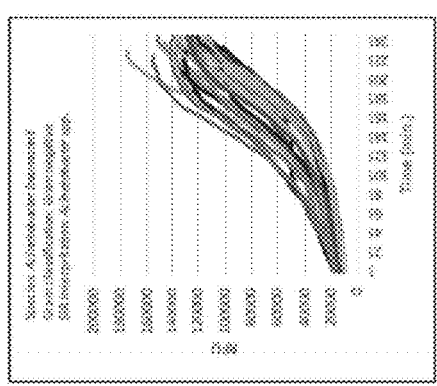
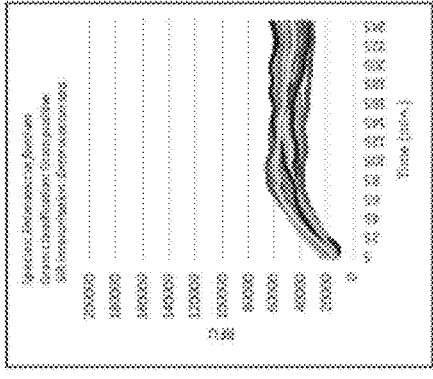
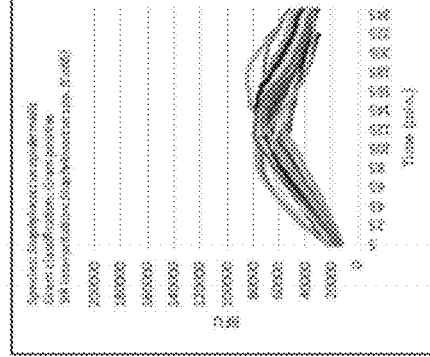
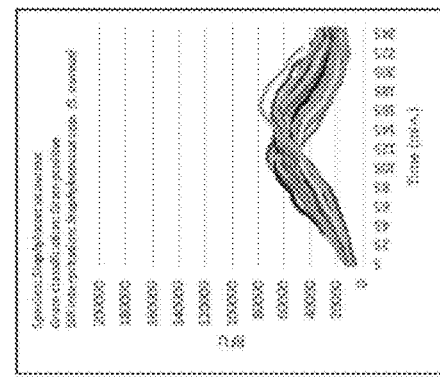
FIG. 18

Pathogen Identification

| Species | Classification | Training Accuracy | Test Accuracy | AST Time |
|---------|----------------|-------------------|---------------|----------|
| Staphylococcus aureus | Staphylococcus spp. | 74/74 (100%) | 25/26 (96%) | 2 hrs |
| Staphylococcus epidermidis | CoNS | 126/126 (100%) | 38/43 (88%) | 2 hrs |
| Enterococcus faecium | Enterococcus spp. | 35/35 (100%) | 12/12 (100%) | 2 hrs |
| Klebsiella pneumoniae | Enterobacteriaceae | 25/25 (100%) | 10/10 (100%) | 3 hrs |
| Escherichia coli | Enterobacteriaceae | 27/27 (100%) | 24/24 (100%) | 3.5 hrs |
| Pseudomonas aeruginosa | Pseudomonas aeruginosa | 68/70 (97%) | 24/24 (100%) | 4 hrs |
| Acinetobacter baumannii | Acinetobacter spp. | 28/31 (90%) | 9/12 (75%) | 4 hrs |
| Total | | 383/388 (98.7%) | 126/135 (93.3%) | 2-4 hrs |

FIG. 20

COMPOSITIONS AND METHODS FOR CELLULAR PHENOTYPE ASSESSMENT OF A SAMPLE USING CONFINED VOLUME ARRAYS

CROSS-REFERENCE TO RELATED APPLICATIONS

This Application is a national phase application under 35 U.S.C. § 371 of International Application No. PCT/US2019/036899, filed Jun. 13, 2019, which claims priority to U.S. Provisional Patent Application Ser. Nos. 62/684,736 filed Jun. 13, 2018 and 62/747,309 filed Oct. 18, 2018, each of which are incorporated herein by reference in their entirety.

TECHNICAL FIELD

This disclosure relates generally to cellular biology and microbiology, and more particularly to compositions and methods for rapid and sensitive phenotypic assessment of cells and the rapid and sensitive characterization of their phenotypic response to compounds and/or treatments.

BACKGROUND

In various instances, Disease-Causing Cells (DCCs) are found in quantities below the limit-of-detection of conventional analytical techniques. Thus, methods for identifying DCCs and characterizing their response to treatment typically require either multiplication of the target cells and/or target-dependent amplification of the target cells' molecular contents and/or products, depending on the application.

Due to high sensitivity compared to other techniques, nucleic acid amplification (e.g., PCR-based) tests (NATs) have become the preferred method for fast pathogen identification. DNA can be amplified from a single copy to billions of copies within hours using PCR.

NATs require complicated sample workflow steps which usually include cell lysis followed by nucleic acid concentration step that also removes PCR inhibitors from the samples. Cell lysis creates an asymmetry in the requirements for nucleic acid extraction efficiency. Mycobacteria and fungi, for example, possess a very thick cell wall compared to gram-negative bacteria and thus are far more difficult to lyse, usually requiring a mechanical lysis step to efficiently disrupt their cell wall. Consequently, NATs that utilize simple chemical lysis methods often lack sensitivity for these tougher pathogens. Furthermore, cell lysis reagents can inhibit PCR reactions because the reagents denature proteins and PCR utilizes proteins to perform the amplification reaction. Therefore, cell lysis introduces the need for highly efficient wash steps to remove lysis reagents from the extracted nucleic acid. In addition, NATs require expensive assay development methods because they rely on pathogen-specific reporter molecules (primers and probes) that must be designed specifically for each target. Each NAT must therefore include an expensive molecular R&D process which involves primer/probe design and screening for each target.

NATs that include two or more targets (multiplexed) cannot simultaneously quantify those targets accurately and precisely. This is because the same nonspecific interactions between reporter species cause variances in the PCR signal output and quantitative PCR relies on reproducible reaction results in order to correlate the generated amplification curves to the initial target concentration. This is a significant limitation because it limits the use of multiplex NATs for the diagnosis of infections from non-sterile infection areas of the body where most infection occur. In non-sterile areas of the body humans are often colonized by the same pathogens that can cause an infection. Because infections are caused by microbes that overwhelm the body's defenses, they will generally produce more colony isolates than commensals will. In non-sterile infection sites, therefore, the number of pathogens present in the clinical sample (the pathogen load) is what determines whether a bacterial species is causing an infection or "peacefully" colonizing the site. For example, in order to definitively diagnose the source of a pneumonia infection from a lower respiratory system (e.g., bronchoalveolar lavage (BAL)) the pathogen load for any bacteria present in the sample must exceed $10^3$ CFU/mL to be considered the source of an infection. Similarly, for urine specimens the threshold is $10^5$ CFU/mL.

Furthermore, if a NAT assay includes more than one target (multiplex assay), requiring more than one reporter species (primer and/or probe pair), the different target and/or reporter species can interact nonspecifically with one another, causing either false positives when the reporter amplifies nonspecifically against the other reagents or false-negatives when the target amplification reaction is inhibited by a non-specific interaction with another species. Consequently, this limits how many targets can be identified within a single NAT. This becomes particularly relevant with the issue of drug resistance because, in the case of gram-negative bacteria and mycobacteria, there are numerous mutations (each mutation being a target) indicative of resistance. NATs can only interrogate a small fraction of those mutations within a single test. In addition, the genes that reside in an organism's genotype may not always contribute to the phenotype. Therefore, genotypic information often portrays an inaccurate or incomplete picture of a pathogen's phenotypic response. Methicillin-resistant *Staphylococcus aureus* (MRSA), for example, often do not express the mecA gene that confers resistance. Therefore, when it comes to the clinically important determination of whether the pathogen causing an infection is susceptible to a particular drug NATs have low clinical validity because these tests can only examine a small fraction of the genetic mutations that can confer antimicrobial resistance and cannot account for epigenetic resistance mechanisms at all.

NATs must also be engineered to interrogate well understood genetic resistance markers. However, microbes continuously evolve new resistance mechanisms under the selective pressure introduced by antimicrobial drugs. By relying on the information that changes over time (the genotype), NATs become less accurate as microbes evolve new resistance mechanisms. In order to keep up with the fundamentally changing landscape of antimicrobial resistance, new resistance mechanisms must be investigated and understood, and new NATs must be developed and must clear regulatory hurdles to enter the clinic. This costly process can take years.

Phenotypic antimicrobial susceptibility testing (AST) remains the gold standard for diagnosing microbial infections because it measures the phenotypic microbial response to the antimicrobial drugs being considered for treatment, and thus relies on functional endpoints that translate directly to the desired clinical response. Being phenotypic, AST encompasses all resistance mechanisms, thus providing high clinical validity.

AST results in the determination of a minimum inhibitory concentration (MIC), which corresponds to the minimum concentration of an antimicrobial needed to significantly inhibit microbial growth. Because different microbes have different intrinsic characteristics that influence their observed response to a given antimicrobial drug, a MIC alone does not inform the clinician whether pathogens are susceptible or resistant to the antibiotic. For example, an oxacillin MIC of 2 µg/mL indicates susceptibility to oxacillin if the pathogen is *Staphylococcus aureus* (which would therefore respond to oxacillin treatment) and resistance if the pathogen is *Staphylococcus epidermidis* (which would therefore not respond to treatment). To interpret any AST result pathogen identification (ID) is required.

AST cannot be accurately carried out if multiple pathogens are present in the same test because microbial growth between species is not distinguishable and the antibiotic response of a species cannot be specifically measured. Furthermore, competition for resources can be enhanced under the selective pressure of an antimicrobial drug, obfuscating the impact of the antimicrobial itself. This is particularly important because most bacterial infections occur in areas of the body that are always populated by bacteria. For infections in non-sterile sites, it is critical to identify and separate the bacteria causing the infection (pathogens) from those that "peacefully" reside at the infection site (commensals). This prevents culturing of the specimen in liquid broth media that are simpler to use and often accelerate microbial growth. Instead, quantitative or semiquantitative culturing is required, which is accomplished by spreading the sample across a petri dish at different concentrations so that at some point on the plate the microbes will grow in isolated colonies of a single species. Plate-streaking also allows lab technician to count visually distinguishable colonies present at a certain concentration to determine whether the microbes in the sample have become invasive. Colonies formed by different species can be distinguished visually from one another and counted. The lab technician can also manually extract a pathogen colony made up of entirely the same species for further testing. Thus, the quantitative/semi-quantitative culturing process not only produces the large number of cells needed for subsequent AST, it also ensures that the bacteria being tested are homogenous and are those causing the infection (pathogens).

However, quantitative/semi-quantitative culturing is highly subjective and error prone, requiring highly skilled technicians to determine which colonies to exclude or include in subsequent testing. Polymicrobial infections are particularly challenging. Often, one of the infecting pathogens is a fastidious organism (an organism that has a complex nutritional requirement and typically only grows under specific conditions) or a slow growing organism and the other is not. The non-fastidious/faster growing organism will often drown out the fastidious/slower-growing organism on a culture plate and conceal its presence in the specimen.

Because AST requires an upfront culture growth step to produce the large number of cells needed for evaluation against drug candidates for treatment, it can take one to five days of incubation on a petri dish to grow the microbial population from the numbers present in the patient sample to the numbers needed for AST, far too slow to effectively guide antibiotic treatment decision, particularly for serious bacterial infections.

Thus, there remains a need for additional methods and apparatus for identifying and characterizing cells in a sample in a fast and/or efficient manner.

SUMMARY

Certain aspects of the methods and/or devices/systems described herein can be practiced using an integrated workflow and analysis that can be automated and performed on a disposable cartridge providing integrated testing without having to utilize one or more kits to perform sample preparation prior to analysis. The compositions and methods described herein address the various problems associated with the current methods for evaluating a sample and the resulting diagnosis or prognosis of a patient. Certain embodiments are directed to methods and analysis that interpret a time-dependent signal produced by, for example, unique cellular metabolism, respiration, growth, and/or permeability attributes of isolated cells. As used herein, metabolism refers to the set of life-sustaining chemical transformations or processes within a cell. The three main purposes of metabolism are the conversion of food/fuel to energy to run cellular processes; the conversion of food/fuel to building blocks for proteins, lipids, nucleic acids, and some carbohydrates; and the elimination of nitrogenous wastes. Respiration as referred to herein is cellular respiration, a set of metabolic reactions and processes that take place in a cell or organism to convert biochemical energy from nutrients into adenosine triphosphate (ATP), and then release waste products.

In certain instances, it is the variation, "shape", or waveform of a signal over time that changes or is unique to a target rather than specific binding of reporter molecules used to generate the presence or absence of a signal. Thus, it is the "system" that acts like a probe rather than an individual reporter molecule or binding moiety.

The methods described herein produce metabolic, respiratory, or reactant/reagent interaction profiles that can be used to evaluate a sample by characterizing the cellular components of the sample. Specifically, just as this method uses a mammalian or microbial cell's unique metabolism, respiration, permeability and/or other characteristics to distinguish between different cellular and microbial species, those same characteristics can be used to determine whether the cell or microbe is susceptible to a particular compound, cytotoxic compound, or antimicrobial, since a compound or an effective drug will alter the cellular metabolism, respiration, permeability or other characteristics.

In certain aspects methods of the invention can interrogate the interactions of a compound(s) or condition(s) with a cell, be it (i) a normal cell for determining toxicity of a compound or condition, or (ii) a pathogenic or disease-related cell for determining therapeutic efficacy of a compound or condition. This method can account for all resistance mechanisms that may confer resistance to a particular cell and, therefore, offers an enhanced clinical validity.

The currently described methods produce evaluation results at significantly faster turn-around-times (<4 to 6 hours (hrs)) than other methods. The increase in speed is accomplished, in part, by the rapid signal concentration made possible in confined volumes which are orders of magnitude smaller than the milliliter and microliter volumes typically used by other methods.

In the methods described herein, individual cells or microbes are isolated or compartmentalized into separate droplets or volumes, enabling quantification to become the simple matter of counting those droplets or volumes associated with a signal indicating the presence of a particular cell or microbe. The shape or change of the signal over time (e.g., a waveform), which is one of the characteristics relied upon for identification and characterization, is orthogonal to the method for quantification—one does not affect the other. Thus, accurate and precise multiplexed identification and quantification is accomplished simultaneously.

Certain embodiments are directed to methods for evaluating a sample comprising: (a) dividing the sample into two or more sub-samples or sample portions, including a control sub-sample and at least one test sample; (b) mixing each sub-sample or sample portion with one or more reagent, one or more reactant, or one or more reagent and one or more reactant forming distinct sub-sample or sample portion mixtures; (c) compartmentalizing each of the sub-sample or sample portion mixtures into a plurality of small volume compartments, wherein some small volume compartments contain one cell or one cellular aggregate; (d) detecting a physical or chemical characteristic of the small volume compartments over time and generating data relative to each compartment; (e) transmitting the data as an input to at least one function optimized using machine learning. In a particular aspect, the method includes (f) transmitting the data as an input to (i) at least one neural network and (ii) a characterizer forming a neural network output and a characterizer output; (g) transmitting the neural network output to a classifier and forming a classifier output; and (h) transmitting the characterizer output and the classifier output to a second neural net, the second neural net forming an analysis output. The sample can be but is not limited to an environmental sample or a biological sample. In certain aspects the biological sample is a patient sample. In certain instances, the patient is a human patient. The biological sample can be bronchoalveolar lavage (BAL), sputum, saliva, urine, blood, cerebrospinal fluid, seminal fluid, stool, swab, scraping, pus, or tissue. In certain aspects, a control sub-sample does not include a reactant and/or does not include a reagent. In certain aspects, one or more sub-sample is mixed with a reagent, a reactant, or a reagent and a reactant. The reactant can be, but is not limited to a nutrient mix, a drug, or a biological. The reagent can be reporter or a signal generating moiety, such as a fluorogenic or luminogenic reagent. In certain aspects, the analysis output is a determination of a clinical endpoint or the like. The clinical endpoint can be, but is not limited to a patient outcome, a minimum inhibitory concentration of a drug, a susceptible or resistant cell, or a prognosis. In certain aspects, the prognosis can be or include the length of hospital stay or subject's risk of adverse event.

Certain embodiments are directed to methods for evaluating a sample comprising: (a) dividing the sample into two or more sub-samples or sample portions, including a control sub-sample and at least one test sample; (b) mixing each sub-sample or sample portion with one or more reagent, one or more reactant, or one or more reagent and one or more reactant forming distinct sub-sample or sample portion mixtures; (c) compartmentalizing each of the sub-sample or sample portion mixtures into a plurality of small volume compartments, wherein some small volume compartments contain one cell or one cellular aggregate; (d) detecting physical or chemical characteristic of the small volume compartments over time and data relative to each compartment; (e) transmitting the collected data as an input to (i) at least one neural network and (ii) a characterizer forming a neural network output and a characterizer output; (f) transmitting the neural network output to a classifier and forming a classifier output; and (g) transmitting the characterizer output, the classifier output, community information, and patient information to a second neural net, the second neural net forming an analysis output. The method can further include a control sub-sample. In certain aspects, one or more sub-sample is mixed with a reagent, a reactant, or a reagent and a reactant. The reactant can be but is not limited to a nutrient mix or a drug. The reagent can be but is not limited to a fluorogenic or luminogenic reagent.

Certain embodiments are directed to methods for evaluating a sample comprising: (a) dividing the sample into two or more sub-samples or sample portions; (b) mixing each sub-sample or portion with one or more reagent and/or one or more reactant forming distinct sub-sample sample portion mixtures; (c) compartmentalizing the sub-sample or sample portion mixtures into a plurality of small volume compartments, wherein some small volume compartments contain one cell or one cellular aggregate; (d) monitoring characteristics of the small volume compartments over time and collecting compartment data; and (e) transmitting the collected data to at least one neural network. The method can further include a control sub-sample. In certain aspects, one or more sub-sample is mixed with a reactant, a reagent, or a reagent and a reactant. The reactant can be but is not limited to a nutrient mix or a drug. The reagent can be but is not limited to a fluorogenic or luminogenic reagent.

In certain aspects a characterizer can include various analysis, manipulation, processing, or determinations of the character of data or measurement of other physical attributes gather or observed from a sample, a confined volume, or other components of the partitions, samples, sub-samples or the like. For example, cell sensitivity to a particular Test Reactant can obtained by quantifying the difference between a partition that includes cells exposed to the reactant, and those that are not. This difference is reflected in the signal differences between the two partitions. Any information not related to classification of an individual waveform is contained in the Characterizer. The Characterizer (CH) can contain but is not limited to global statistics of both populations such as the average intensity of each compartment. In certain instances, N2 uses the classified waveforms in the classifier (CL) and the population statistics in CH for both test sample (TS) and control sample (CS) to compute a clinical endpoint. Non-limiting examples of inputs into and outputs from the Characterizer include, but are not limited to outputs—(i) Average max signal of all the waveforms in a partition, (ii) Area under the curve for all the waveforms in a partition; (iii) Average max derivative for all the waveforms in a partition; (iv) Average point in time when each waveform cross a particular threshold value for all the waveforms in a partition; (v) Same as above using "median" instead of "average"; (vi) Same as above except for using normalized waveforms, where each waveform is divided by the average signal at the same time-point of the waveforms in a negative compartments (compartments without cells) within the same partition.

In certain aspects, the Classifier (CL) identifies to which of a set of categories a waveform from a single compartment belongs based on a training set of observations whose category membership is known. Examples of inputs into the Classifier include (i) Raw waveforms and/or (ii) Dimensionally reduced waveforms, in addition to the above inputs with patient information, community information, and/or imaging data. The methods of the invention are compatible with any statistical classification method based on supervised learning, including neural networks, linear vector quantization, linear classifiers, support vector machines, quadratic classifiers, decision trees, kernel estimation, and meta-algorithm approaches. Certain aspects use one or more neural networks.

Disease causing cells (DCCs) are defined herein as either host cells, such as malignant or disease-associated cells of the host from which the sample is taken (e.g., cancer cells), or acquired cells (e.g., fungal or bacterial), which include any microflora associated with, involved in, implicated in, or indicative of a disease or pathology. Such diseases include but are not limited to cancer and infections.

As used herein the term "sample partition" or "partition" refers to a portion of a sample. A sample can be partitioned into a number of partitions, or sub-sample volumes. Each partition can bet processed, treated, manipulated, and/or incubated separately and under distinct or similar conditions.

As used herein, the term "compartment" refers to a volume of fluid (e.g., liquid or gas) that is a separated portion of a bulk volume (e.g., a sample). A bulk volume may be compartmentalized into any suitable number (e.g., $10^2$, $10^3$, $10^4$, $10^5$, $10^6$, $10^7$, etc.) of smaller volumes or compartments. Compartments may be separated by a physical barrier or by physical forces (e.g., surface tension, hydrophobic repulsion, etc.). Compartments generated from the larger volume may be substantially uniform in size (monodisperse) or may have non-uniform sizes (polydisperse). Compartments may be produced by any suitable manner, including emulsion, microfluidics, and micro spray methods. One example of compartments are droplets.

As used herein, the term "droplet" refers to a small volume of liquid which is immiscible with its surroundings (e.g., gases, liquids, surfaces, etc.). A droplet may reside upon a surface, be encapsulated by a fluid with which it is immiscible, such as the continuous phase of an emulsion, a gas, or a combination thereof. A droplet is typically spherical or substantially spherical in shape but may be non-spherical. The shape of an otherwise spherical or substantially spherical droplet may be altered by deposition onto a surface. A droplet may be a "simple droplet" or a "compound droplet," wherein one droplet encapsulates one or more additional smaller droplets. The volume of a droplet and/or the average volume of a set of droplets provided herein is typically less than about one microliter, for example droplet volume can be about 1 µL, 0.1 µL, 10 µL, 1 µL, 100 nL, 10 nL, 1 nL, 100 fL, 10 fL, 1 fL, including all values and ranges there between. The diameter of a droplet and/or the average diameter of a set of droplets provided herein is typically less than about one millimeter, for example 1 mm, 100 µm, 10 µm, to 1 µm, including all values and ranges there between. Droplets may be formed by any suitable technique, including emulsification, microfluidics, etc., and may be monodisperse, substantially monodisperse (differing by less than 5% in diameter or volume), or polydisperse.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

In the following discussion and in the claims, the terms "including" and "comprising" are used in an open-ended fashion, and thus should be interpreted to mean "including, but not limited to . . . ." Also, the term "coupled", "link" or "points to," and forms thereof, are intended to mean either an indirect or direct connection. Thus, if a first component links or couples to a second component, that connection may be through a direct connection or through an indirect connection via other components and connections.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

For a more complete understanding of the present disclosure, and the advantages thereof, reference is now made to the following descriptions taken in conjunction with the accompanying drawings, in which:

FIG. 8A-8B (8A) schematically illustrates an embodiment of FIG. 6B where the cell reactants are different nutrient mixes and a single cell reagent is used; (8B) schematically illustrates an embodiment of FIG. 7B where the cell reactant is a nutrient mix and the cell reagents are different combination of viability dyes, fluorogenic substrates, and luminogenic substrates.

FIG. 15 illustrates using shear stress for droplet generation or using Laplace pressure gradients for droplet generation.

FIG. 18 illustrates waveforms representing various bacterial species.

FIG. 20 illustrates an example of results from pathogen identification studies.

DETAILED DESCRIPTION

Figure 1:
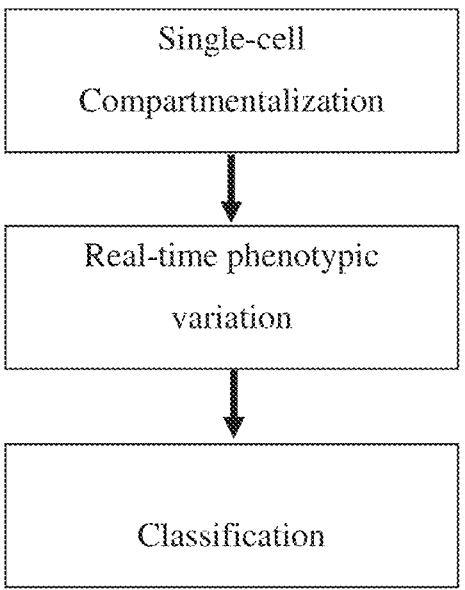
FIG. 1 illustrates the general concept for rapid phenotypic diagnosis and screening. Individual cells are compartmentalized so that the observable changes in the compartment represent the functional characteristics of the encapsulated cell. Functional variation is recognized and used to classify the encapsulated cell.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of that embodiment, and not intended to intimate that the scope of the disclosure, including the claims, is limited to that embodiment.

Certain aspects of the invention generally relate to methods for sample characterization using single-cell analysis. Sample characterization can be used to diagnose a condition or disease state or to assess and characterize cell phenotypes in the sample, for instance drug susceptibility or resistance. The following sections discuss general considerations for methods of producing and analyzing cellular phenotypes by using compartmentalization of a sample or its sub-samples (i.e., partitions). In certain aspects reagent-free, optical, luminescent, fluorogenic, luminogenic, or other signals can be analyzed and characterized using neural networks and other methods of data analysis.

Analytical methods include the use of artificial intelligence (AI). AI can be used to analyze and/or compare one or more sample to determine one or more cellular phenotypes in a sample. In certain aspects the cellular phenotype(s) can be use in identifying, diagnosing, prognosing, or characterizing a subject or a sample from a subject. The methods can be optimized for any clinical endpoint, such as patient outcomes, minimum inhibitory concentration, susceptible or resistant, prognoses such as length of stay, patient risk, etc.

The general concept for rapid phenotypic diagnosis and/or screening includes compartmentalizing individual cells or cellular aggregates so that the observable changes in the compartment represent the functional characteristics of the compartmentalized or encapsulated cell. Variation in cellular function is assessed and/or characterized, and this functional variation or phenotype is used to classify the cell.

Single-cell compartmentalization. Due to the limited-diffusion environment, compartmentalization or encapsulation within a pico-scale (sub-nanoliter) compartment drastically enriches the concentration of cell components and products within the reaction volume, allowing cell outputs to achieve detectable concentrations much faster than within typical reaction volumes. A single cell in a 500 pico-liter reaction volume, for example, is equivalent to 2 million cells in a milliliter reaction volume. Consequently, compartmentalization allows cell outputs to be observed much sooner and more sensitively than in traditional volumes.

Similarly, the encapsulated or compartmentalized cell can rapidly influence the environmental conditions within the pico-scale compartment. Changes in the compartment's pH or redox potential, for example, will be governed by the encapsulated cell or daughter cells (the result of one or more cell divisions).

Some single-celled microorganisms cannot always be isolated as individual cells, notably bacteria such as *Staphylococcus aureus* which often present in monoclonal cell aggregates or clusters after cell division. Cell clustering is, in fact, a phenotypic trait that can be used to distinguish clustering organisms from those that do not cluster. Furthermore, the aggregated cells need not be distinguished therapeutically because they will generally respond to the same therapies, drugs, or conditions.

Real-time phenotypic variation. At pico-scale volumes, observable changes in the compartment are dominated by the cell phenotype, including the metabolome, transcriptome, proteome, or environmental variation, examples include:

Metabolome variation. The metabolome comprises the complete set of molecules in the compartment that undergo a chemical transformation in the presence of a live cell, including cell reagent(s) that are compartmentalized along with the cell, including enzyme substrates.

Enzyme substrates comprise any substance catalyzed or modified by an enzyme in the compartment's proteome or transcriptome (protein or RNA). Substrate variation is distinguished here from the proteomic and transcriptomic variation because it is inherently more multi-dimensional.

Substrate reaction rates depend on solution conditions, substrate concentration, and the substrate's access to the enzyme's active site. For example, an enzyme substrate may need to permeate the cell wall and/or membrane to access an enzyme within a cell. Because cell permeability can vary between species, the substrate concentration varies characteristically over time in two compartments encapsulating different cell species even if the proteome and the environment are identical in both compartments.

Finally, while metabolomic variation often includes substrate variation, it should be clear that substrate variation includes enzymes and reagents that do not participate in the cell's metabolic pathways, including any reagent introduced into the compartment that undergoes an enzymatically catalyzed chemical transformation.

Transcriptome variation. The transcriptome comprises the complete set of RNA transcripts in the compartment, including messenger RNA (mRNA) and micro-RNA (miRNA). The concentration of an RNA transcript will vary according to the cell's phenotype and can be used to classify the compartmentalized cell. Micro-RNA is often secreted and can be probed from outside the cell, concentrating quickly in the pico-scale environment and obviating the need for cell permeable detection reagents.

Proteome variation. The proteome comprises the complete set of proteins in the compartment. The compartment's proteomic composition will vary in the presence of a live cell according to the cell phenotype. The proteome can include proteins expressed from foreign or heterologous genes introduced into the cell through transformation, transfection, and transduction.

Environmental variation. Environmental variation comprises any change to the compartment's temperature, pH, and redox potential. At pico-scale volumes, environmental variation is governed by the interaction between the cell and the cell reactants that are compartmentalized along with the cell.

Classification. Single-cell compartmentalization ensures that the phenotypic changes observed in a compartment are characteristic of a single cell species rather than an average of multiple species. These changes can then be classified into useful information using statistical data analysis. The method of the invention is compatible with statistical approaches that rely on both supervised learning and unsupervised learning.

Phenotypic diagnosis based on supervised learning. Classification is the problem of identifying to which of a set of categories a phenotypic observation belongs based on a training set of observations whose category membership is known. Classification is considered an instance of supervised learning where a training set of correctly identified observations is available. An example is assigning a diagnosis to a given patient based on the observed characteristics of a patient sample using a function optimized using previous observations under relevant conditions. The methods of the invention are compatible with any statistical classification method based on supervised learning, including neural networks, linear vector quantization, linear classifiers, support vector machines, quadratic classifiers, decision trees, kernel estimation, and meta-algorithm approaches. Certain aspects use one or more neural networks.

Phenotypic diagnosis based on unsupervised learning. Statistical analyses based on unsupervised learning are useful in instances when relative categorization possesses predictive value. For example, if multiple drugs are tested on a single cell species, the relative impact of each drug may predict the best drug candidate(s).

Figure 2:
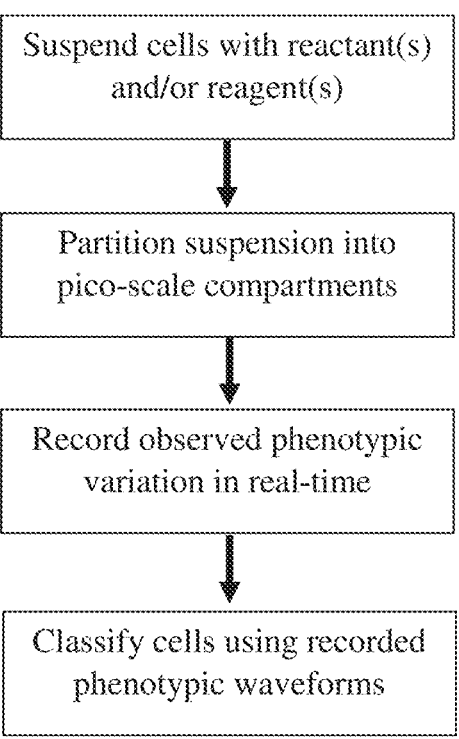
FIG. 2 illustrates the incorporation of the general concept of FIG. 1 into the methods described. Live cells are suspended with cell reagents and cell reactants. The suspension is partitioned into pico-scale compartments that are observable in real-time. Observed changes for each compartment are recorded into a waveform that can be classified into useful information about the encapsulated cell.

Rapid Phenotype Assessment. FIG. 2 diagrams a method for rapid phenotypic diagnosis. Live cells are suspended with cell reagents and/or cell reactants. The suspension is compartmentalized into pico-scale compartments that are observable in real-time. Observed changes for each compartment are recorded into a waveform that can be classified into useful information about the encapsulated cell. The term "cell reagents" includes any substance or mixture of substances used to observe phenotypic variation. Cell reagents act as indicators or detectors of conditions in the compartment without altering or modifying the metabolism or phenotype of a cell. Cell reagents include viability dyes, fluorogenic enzyme substrates, and luminogenic enzyme substrates. The term "cell reactants" includes any substance or mixture of substances used to induce phenotypic variation—essentially any substance that interacts with the cell that is not directly measured during analysis. Cell reactants can influence or modify the metabolism or phenotype of a cell. Cell reactants include cell nutrients, antimicrobial drugs, and cytotoxic drugs. Cell nutrients include, but are not limited to culture media, buffers, salts, gases (e.g., $O_2$ and $CO_2$), hormones, or the like. Cell nutrients also includes any carbohydrates, sugars, and alcohols such as ribitol/adonitol, glucose, maltose, mannose, palatinose, sucrose, galactose, ribose, raffinose, trehalose, gentiobiose, lactose, melibiose, rhamnose, sorbose, turanose, xylose, and/or melizitose. Cell reactants can also include enzyme inhibitors and the like. Drugs include, but is not limited to small molecules, antimicrobial drugs, chemotherapeutic drugs, cytotoxic drugs, bacteriophages, peptides, nanoparticles, CRISPR-CAS 9-based therapeutics, immunotherapies, and the like.

Figure 3:
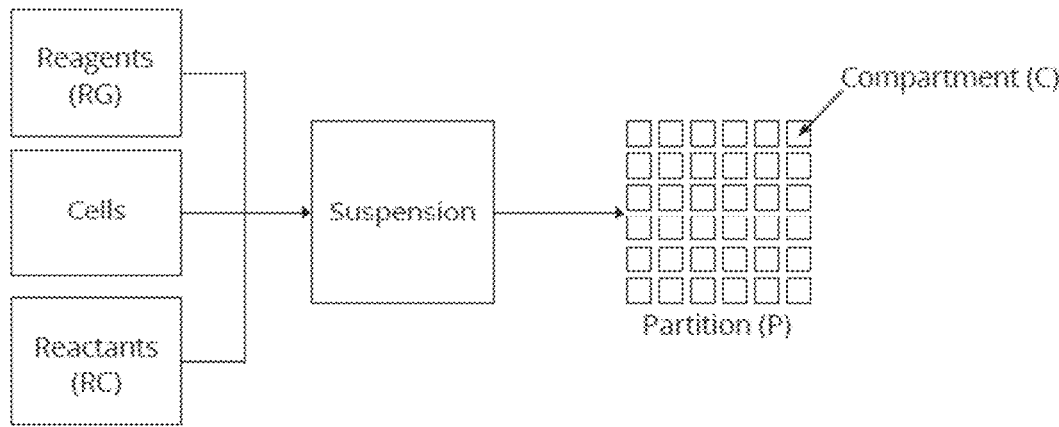
FIG. 3 schematically illustrates separating a cell suspension or sample into multiple compartments.
Figure 4:
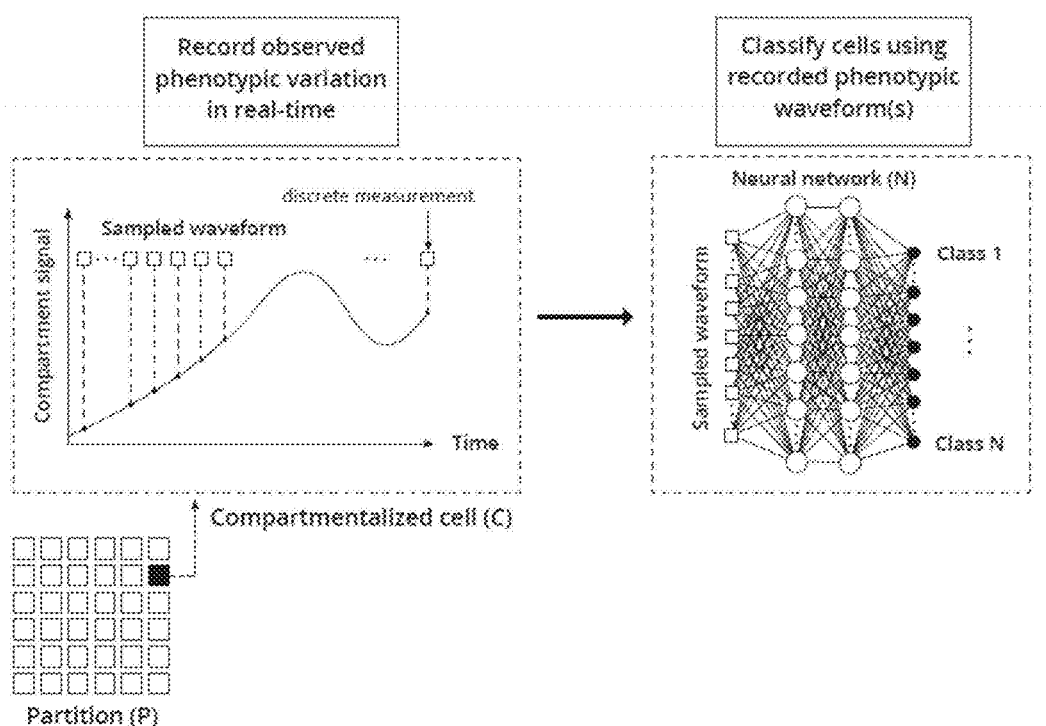
FIG. 4 (left) illustrates an observable compartment signal is sampled and recorded over time. Empty compartments will produce repeatable background signals over time. Compartments with cells in them will generate real-time changes that are different than those generated from empty droplets or from compartments with different cell phenotypes; (right) The recorded signal waveforms are fed into a classification function, in this case a neural network, that classifies each compartmentalized cell based on the sampled waveform.

In various aspects a sample is partitioned or compartmentalized (FIG. 3). A sample or cell suspension can be processed into multiple compartments. Each compartment is then characterized (FIG. 4). On the left side of FIG. 4, an observable compartment signal is sampled and recorded over time. Empty compartments will produce repeatable background signals over time. Compartments with cells in them will generate real-time changes that are different than those generated from empty droplets or from compartments with different cell phenotypes. The recorded signal waveforms are fed into a classification function, in this case a neural network, that classifies each compartmentalized cell based on the sampled waveform.

Figure 5:
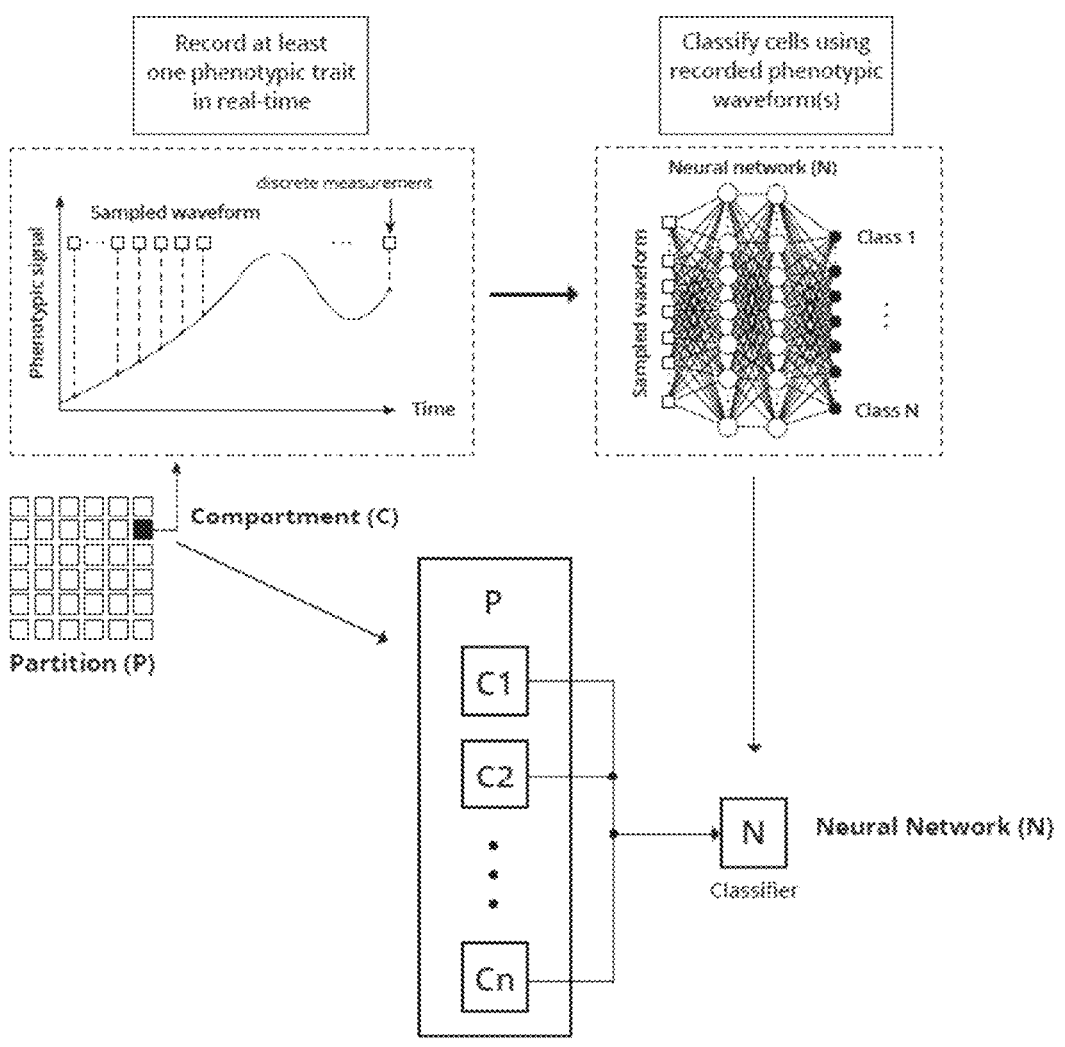
FIG. 5 illustrates the basic embodiment of sampling and recording of a phenotypic waveform from an individual compartment within a partition or sub-sample and feeding the recorded waveform into a deep neural network for classification. The bottom is a schematic illustration of the basic embodiment described above.

FIG. 5 illustrates a basic embodiment of methods described herein. FIG. 5 illustrates one example of the sampling and recording of a phenotypic waveform from an individual compartment within a partition (sub-sample or portion of the sample) and feeding the recorded waveform into a deep neural network for classification.

Figures 6A, 6B, 6C:
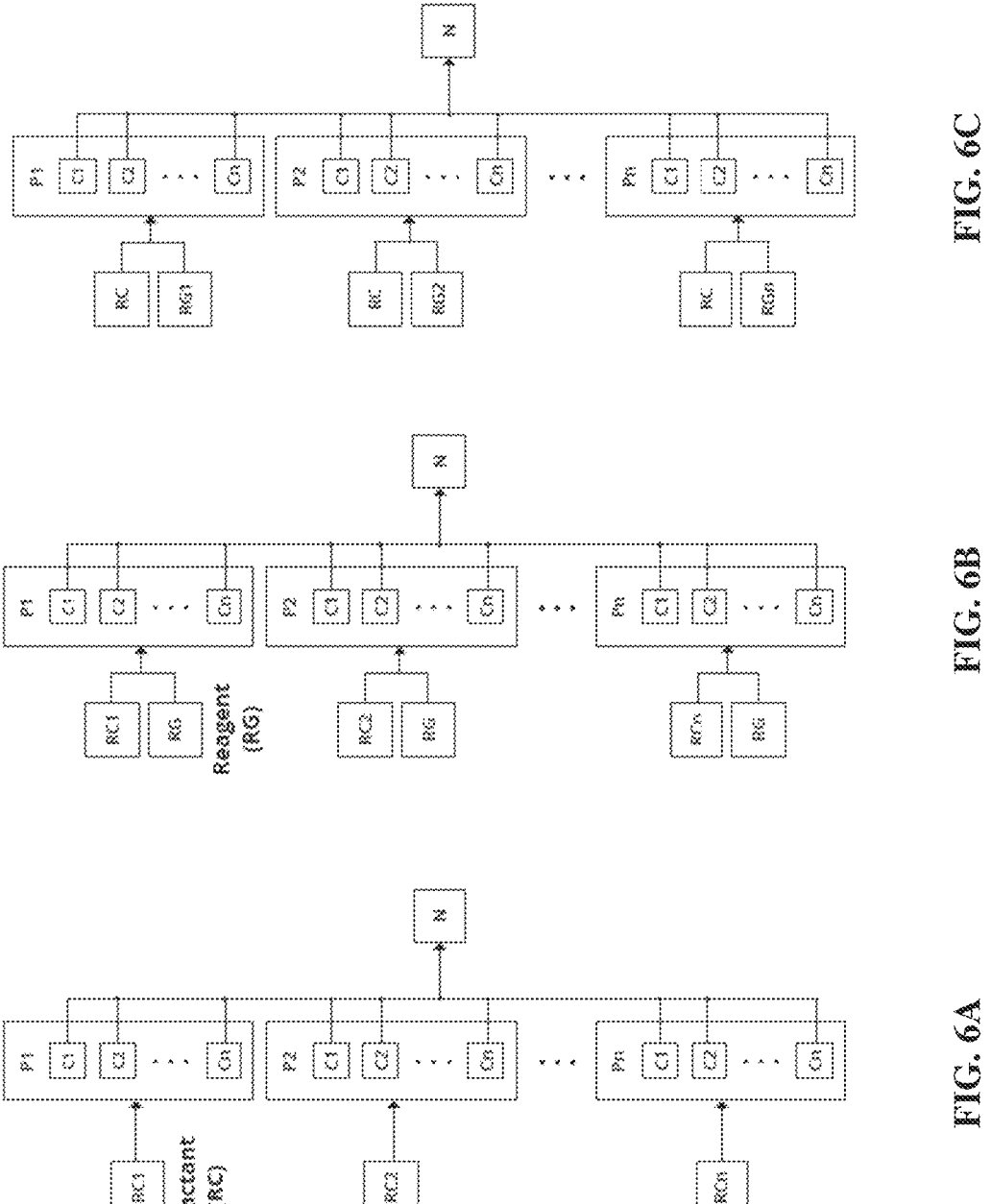
FIG. 6A-6C (6A) is a schematic illustration of one embodiment of the invention that utilizes multiple partitions or sub-samples, each with its own reactant mixture to increase phenotypic variation for a given sample or to account for the nutrient needs of different cell types. This embodiment can be reagent-free as described in more detail below; (6B) is a schematic illustration of a similar embodiment to (6A) but with cell reagents included; (6C) is a schematic illustration of an embodiment with partitions that share the same cell reactants but include different cell reagents.
Figure 21:
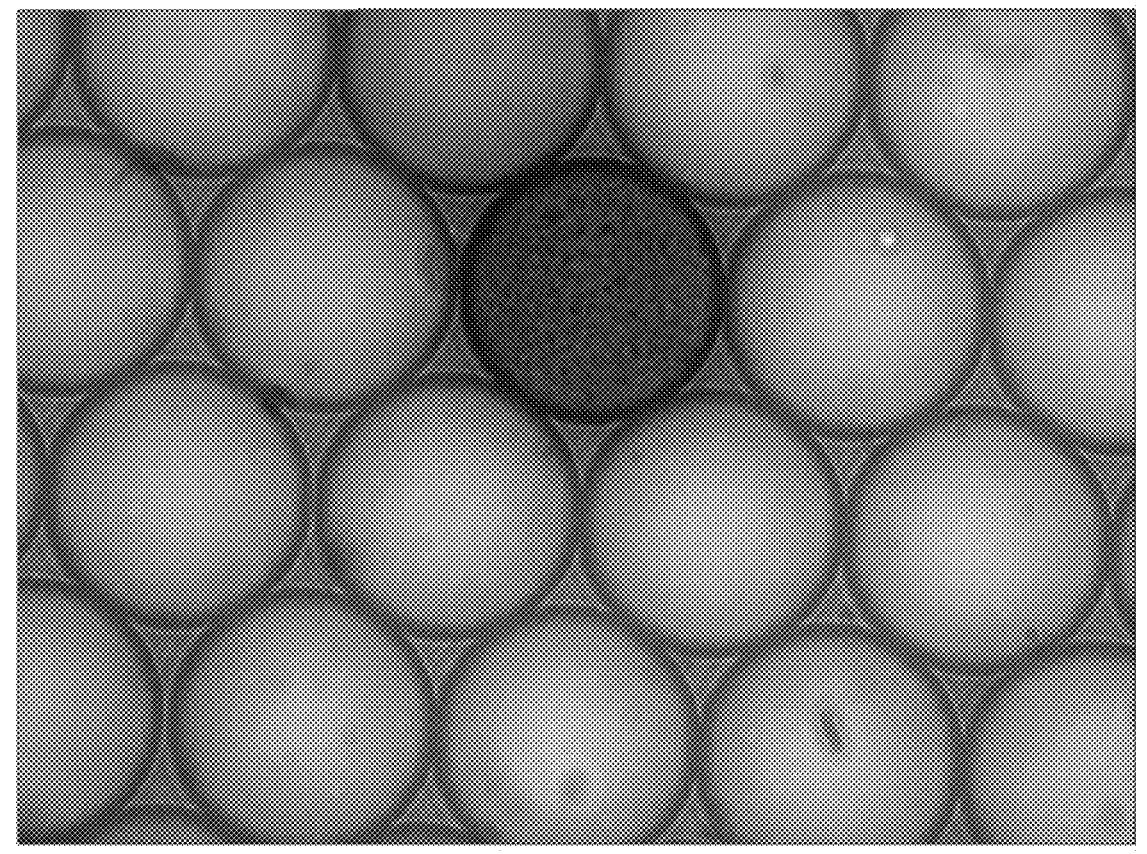
FIG. 21 is a 40× microscope image of an 80 μm droplet that initially contained a single Klebsiella pneumoniae bacterium. After more than 12 hrs incubation at 37° C. the bacterial growth in the droplet almost entirely blocks light transmission through the droplet.

FIG. 6 illustrates various schemes that can be performed using one or more reagents and/or one or more reactants. FIG. 6A illustrates a method that utilizes multiple partitions, each with its own reactant mixture to increase phenotypic variation for a given sample or to account for the nutrient needs of different cell types. In particular embodiments the scheme is reagent-free. FIG. 6B is a schematic illustration of a similar embodiment to FIG. 6A used in conjunction with cell reagents. FIG. 6C is a schematic illustration of a scheme with partitions that share the same cell reactants but include different cell reagents. Methods capable of reagent free detection include:

Optical density of the compartment. As cells grow, they will impact the optical density (OD) of the compartment will vary depending on growth characteristics of the cell and those growth characteristics as determined by OD could be used to classify the cell, see for example FIG. 21). OD method is particularly well suited for a two-dimensional droplet array using simple brightfield microscopy.

Spectral absorbance of the compartment. There are many ways to accomplish spectroscopy. In a basic approach, a sample is exposed to a white beam source and a detector is used to establish a baseline and then the emitter/detector assembly scans across a two-dimensional array of droplets and an absorption spectrum is obtained by comparing the transmitted spectra to the baseline.

Redox potential or pH. Compartmentalization methods that involve etching compartments into silicon can incorporate circuitry to measure the changing redox potential and pH of the compartment.

Figures 7A, 7B, 7C:
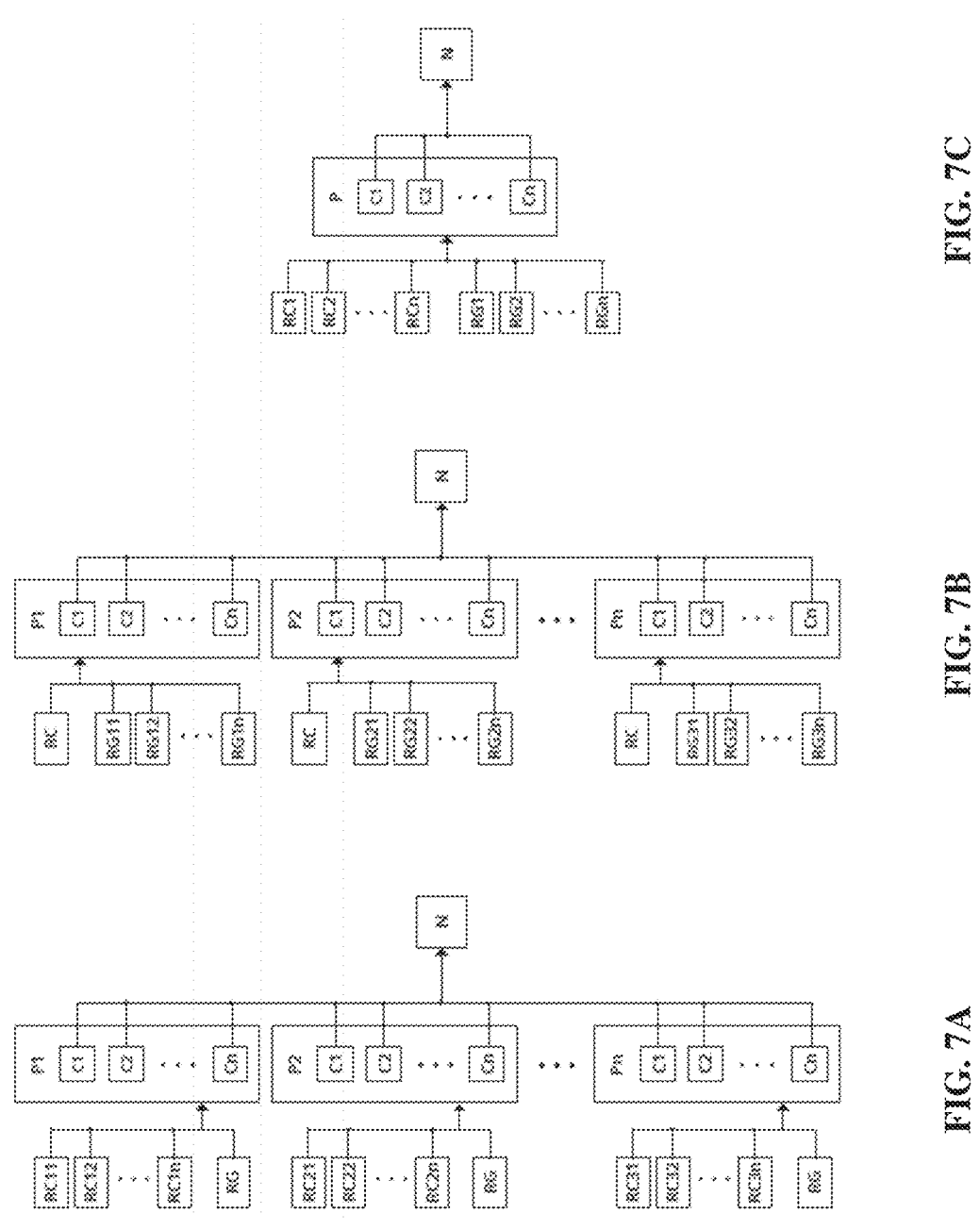
FIG. 7A-7C are schematics illustrating methods that include a combination of cell reactants and cell reagents across one or more partitions.

Certain schemes can use multi-reagent and multi-reactant partitions. FIG. 7A to FIG. 7C are schematics illustrating schemes that include a combination of cell reactants and cell reagents across one or more partitions. One particular scheme is illustrated in FIG. 8. FIG. 8A illustrates one embodiment of the scheme illustrated in FIG. 6B where the cell reactants are different nutrient mixes and a single cell reagent is used. FIG. 8B illustrates one embodiment of the scheme illustrated in FIG. 7B where the cell reactant is a nutrient mix and the cell reagents are different combination of viability dyes, fluorogenic substrates, and luminogenic substrates.

Figure 9:
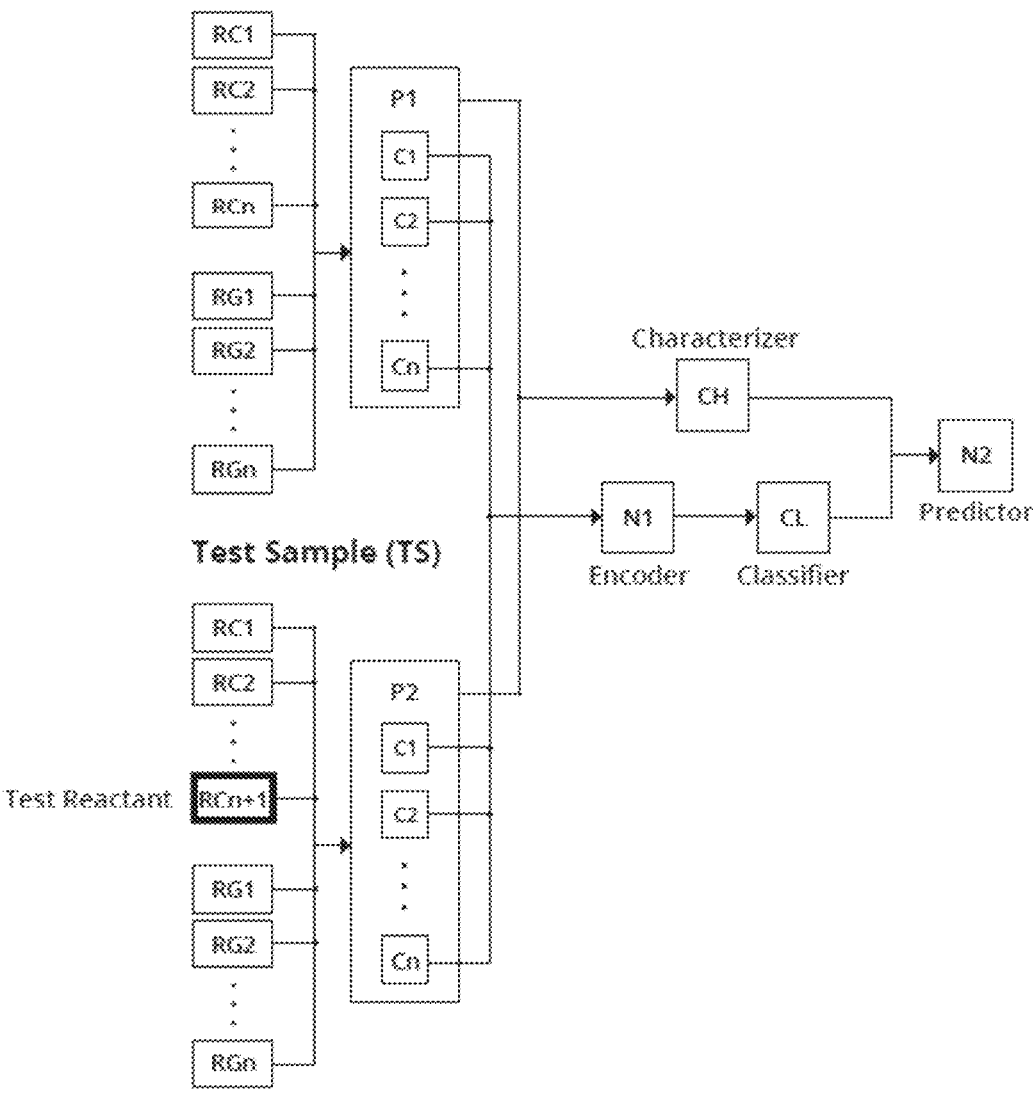
FIG. 9 is a schematic of a diagnostic test for evaluating the impact of a cell reactant on a cell species. The Test Reactant (TR) is only present in the Test Sample (TS) which is otherwise identical to the Control Sample (CS) partition. N1 is an encoder that compresses the full waveforms down into a sparse representation which is then classified by CL. The Characterizer (CH) contains global statistics of both populations such as the average intensity of each compartment, for example. N2 uses the classified waveforms in CL and the population statistics in CH for both TS and CS to compute a clinical endpoint.

In certain aspects the methods described herein can be used for rapid phenotypic testing of a cell reactant, such evaluating test substance for an effect on cell. FIG. 9 is a schematic of a diagnostic test for evaluating the impact of a cell reactant on a cell species. The Test Reactant (TR) is only present in the Test Sample (TS) which is otherwise identical to the Control Sample (CS) partition. N1 is an encoder that compresses the full waveforms down into a sparse representation which is then classified by CL. The Characterizer (CH) contains global statistics of both populations such as the average intensity of each compartment, for example. N2 uses the classified waveforms in CL and the population statistics in CH for both TS and CS to compute a clinical endpoint.

Figure 10:
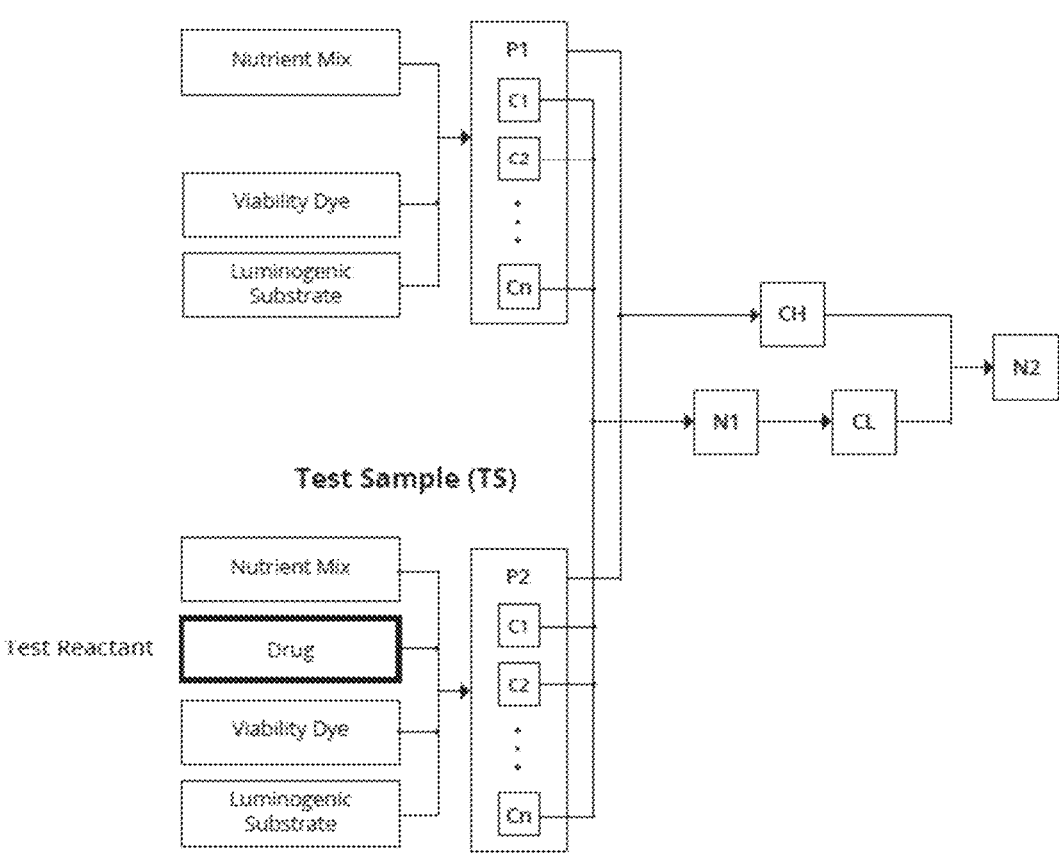
FIG. 10 is a schematic of an embodiment where the Test Reactant in FIG. 9 is a drug. Here N2 utilizes the classified waveforms in CL and the population statistics in CH to compute a clinical endpoint associated with prescribing drug that interacts with the cells being tested. Using machine learning, the neural network N2 can be trained to any clinical endpoint.

FIG. 10 is a schematic of scheme where the Test Reactant in FIG. 9 is a drug. Here N2 utilizes the classified waveforms in CL and the population statistics in CH to compute a clinical endpoint associated with prescribing a drug that interacts with the cells being tested. Using machine learning, the neural network N2 can be trained to any clinical endpoint. Examples include patient diagnosis, patient prognosis, and the like.

Patient Diagnosis. One advantage of the methods described herein is that it allows a diagnostic test to be directly optimized to any clinical endpoint that is relevant to the cells being tested.

Minimum Inhibitory Concentration (MIC). In microbiology, the minimum inhibitory concentration (MIC) is the lowest concentration of a chemical that prevents visible growth of a microbe. MIC information can be used to calculate an optimal dose for a given antimicrobial, depending on the site of infection.

Susceptible, Intermediate, or Resistant (SIR). In microbiology, a MIC result is interpreted as susceptible (or sensitive), intermediate, or resistant for a given pathogen-antimicrobial combination by using cutoff points specific to that combination. MIC cutoffs are established by CLSI guidelines for each pathogen class. Traditionally, an antimicrobial susceptibility test (AST) produces a MIC for a given antimicrobial drug and a separate test is used to identify (ID) the pathogen being tested. The pathogen ID is used to establish the SIR cutoffs for the antimicrobial drug being tested. Only after the ID is known can the cutoffs be established to understand whether the MIC indicates resistance or susceptibility.

An advantage to the method described herein is that the information in the CS sample can be used to simultaneously establish a MIC and SIR cutoffs without requiring an intermediate ID step that translates the waveforms in the CS into a taxonomic classification. This enables the entire system to be optimized to the clinical endpoint (SIR) rather than two intermediary steps.

Pharmacodynamics. Antimicrobial MICs are normally a way of predicting pharmacodynamics of the drug. The MIC is a measure of the potency of an antimicrobial drug. Isolates of a particular species will have varying MICs; sensitive strains will have relatively low MICs, and resistant strains will have relatively high MICs. The breakpoint MIC is the MIC that separates sensitive and resistant strains, and it was traditionally selected on its ability to distinguish two disparate populations: one population with MICs at less than the breakpoint (i.e., susceptible) and one with MICs at more than the breakpoint (i.e., resistant).

Another attribute of the breakpoint MIC is correspondence to achievable serum drug levels using standard dosing. To guide dosing strategy MIC can be combined with intrinsic antibiotic information such as whether the antimicrobial drug is time-dependent or concentration dependent.

Patient Antibiogram. An antibiogram is an SIR result for each antibiotic in a set of antimicrobials being considered for treatment, thus providing an overall profile of antibiotic susceptibility testing results of a specific microorganism to a battery of drugs. A plurality of drugs can be used and each profile for each drug documented.

Chemosensitivity Testing and Mammalian Cell Diagnosis. The methods described above for antimicrobial susceptibility testing are directly applicable to chemosensitivity or drug sensitivity for cancer as well as for tissue-based diseases where the tissue/cells can be isolated and exposure or contact with a drug alters cellular characteristics.

Figure 11:
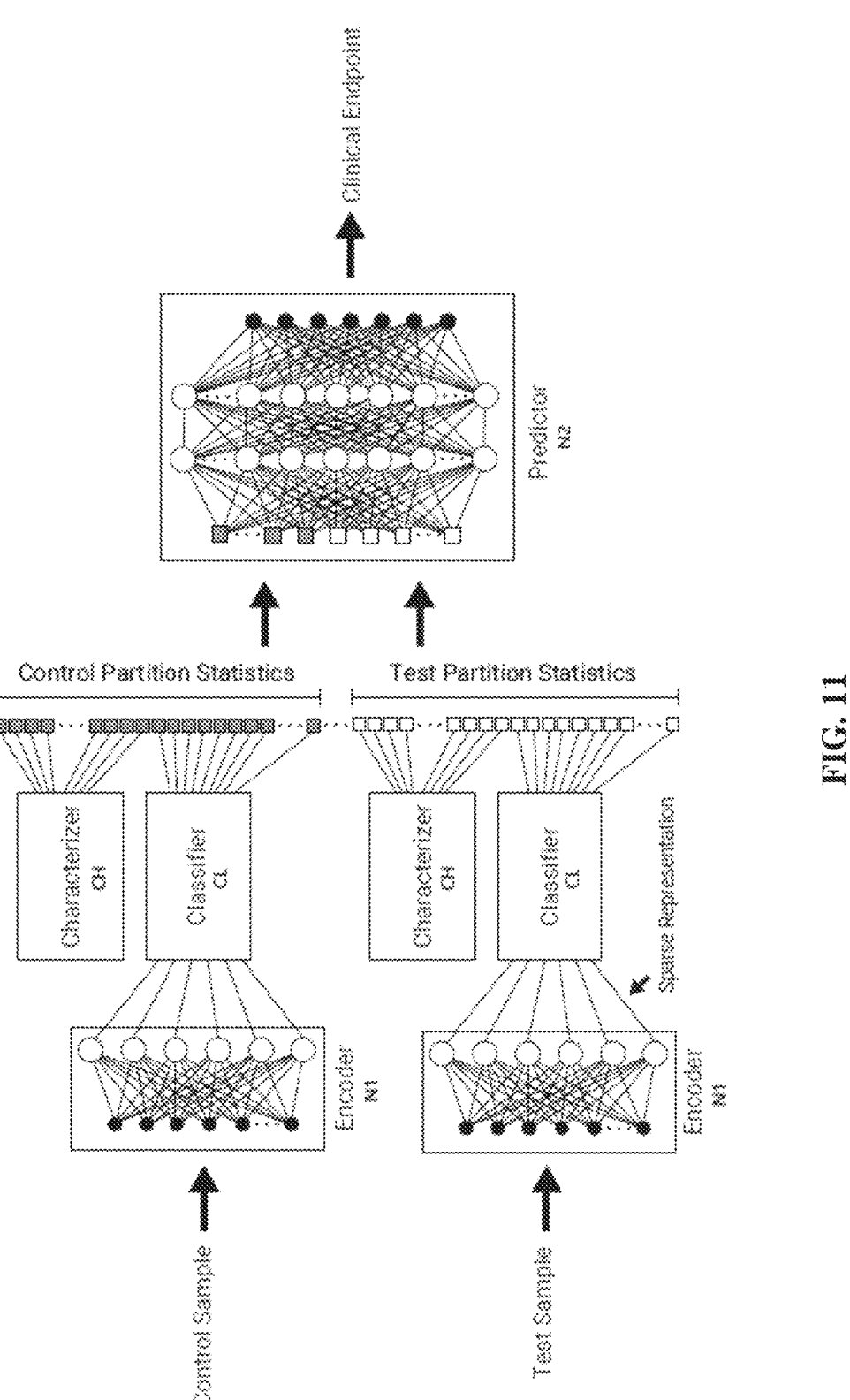
FIG. 11 shows that both the control and test partition or sub-sample waveforms can be fed into the same N1, CH, and CL, but the resulting statistics are fed into separate input nodes of the Predictor neural network, allowing for a detailed comparison of the variation present in CS and TS.
Figure 12:
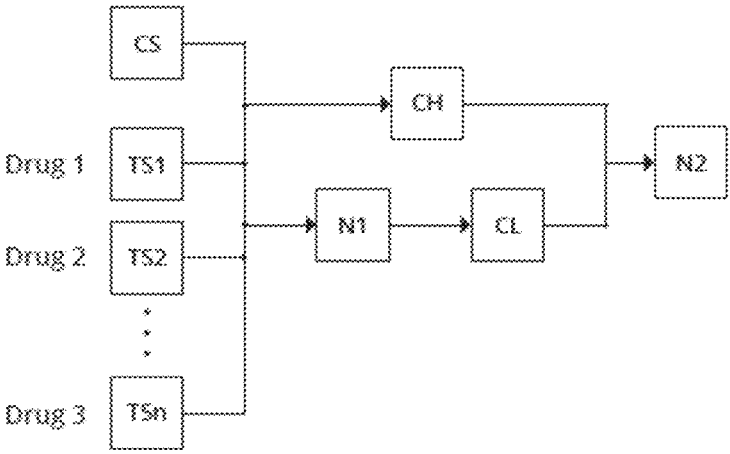
FIG. 12 is a schematic of an example of the embodiment described in FIG. 10 for multiple drugs.
Figure 13:
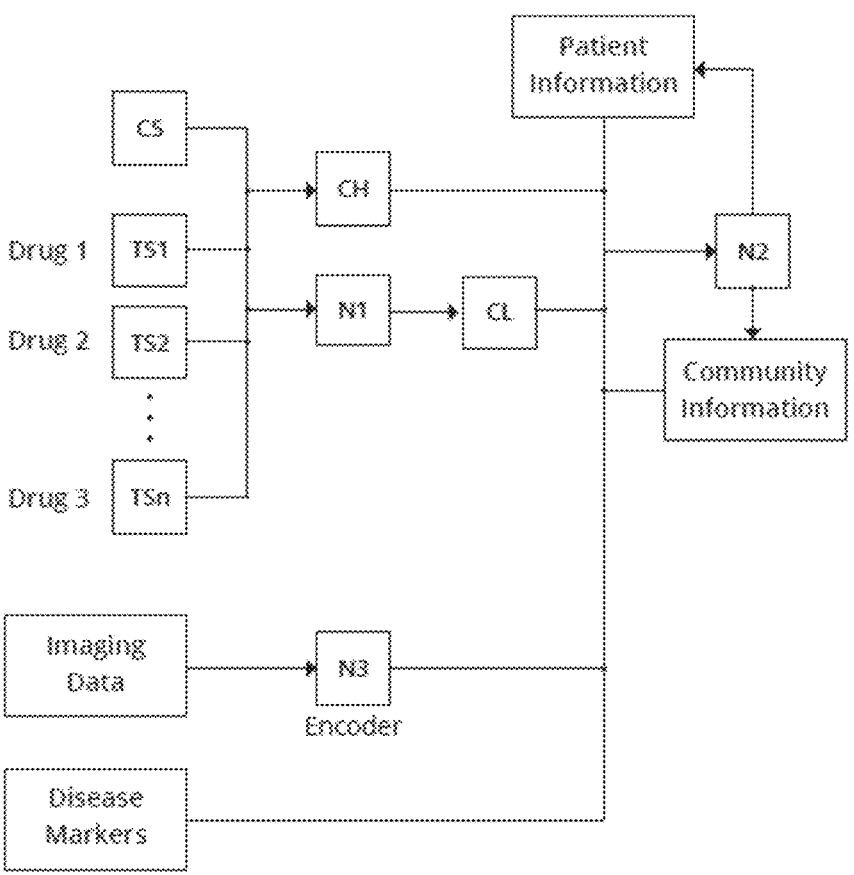
FIG. 13 illustrates a method for optimizing diagnosis using machine learning using sample partition statistics combined with other laboratory results, patient information, and community information to arrive at the most accurate and comprehensive diagnosis and prognosis.
Figure 14:
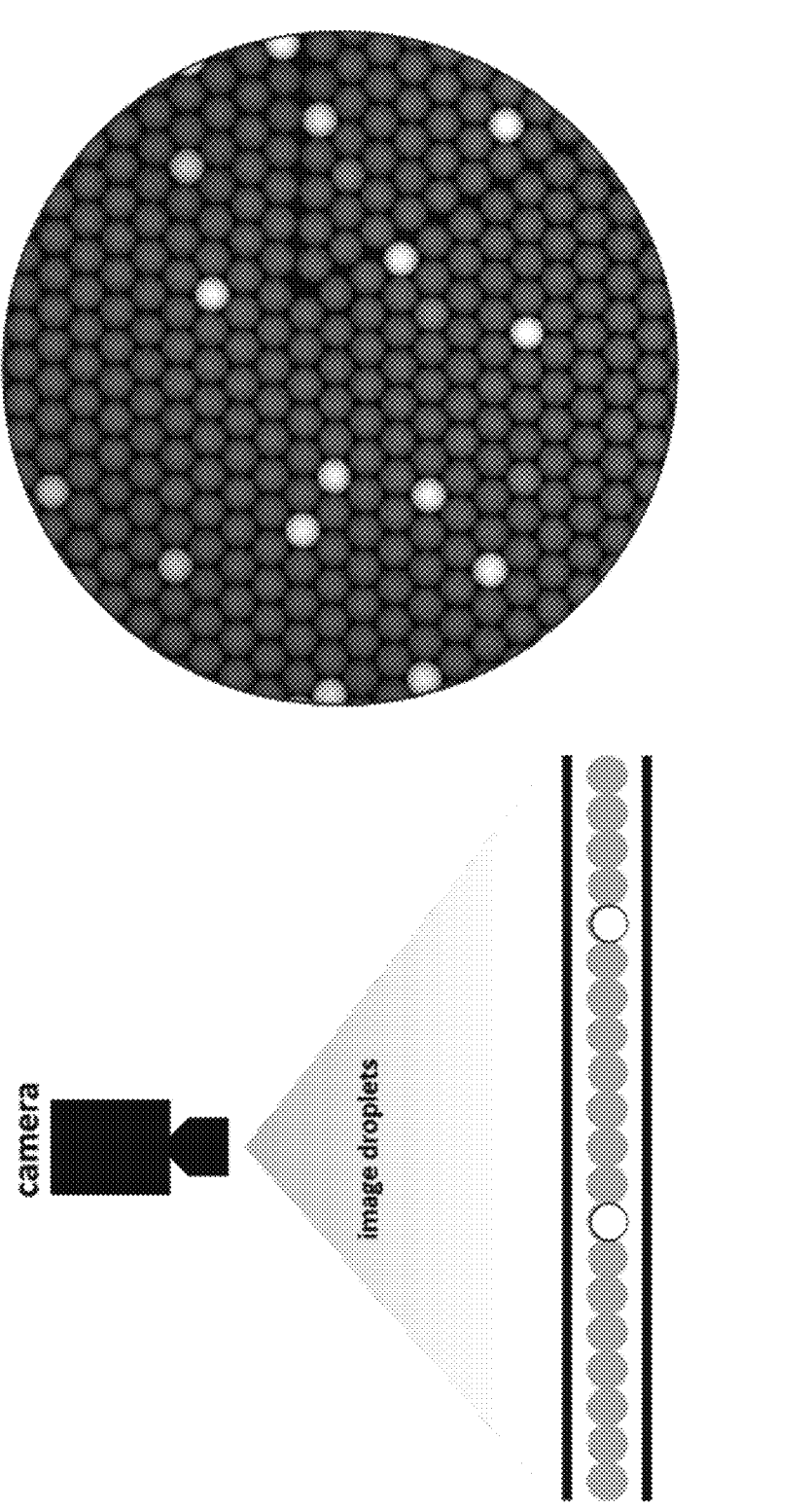
FIG. 14 is an illustration of a droplet monolayer being imaged by a camera and an overhead view of a droplet monolayer. The droplet monolayer provides for good thermal conductivity and temperature control.
Figure 16:
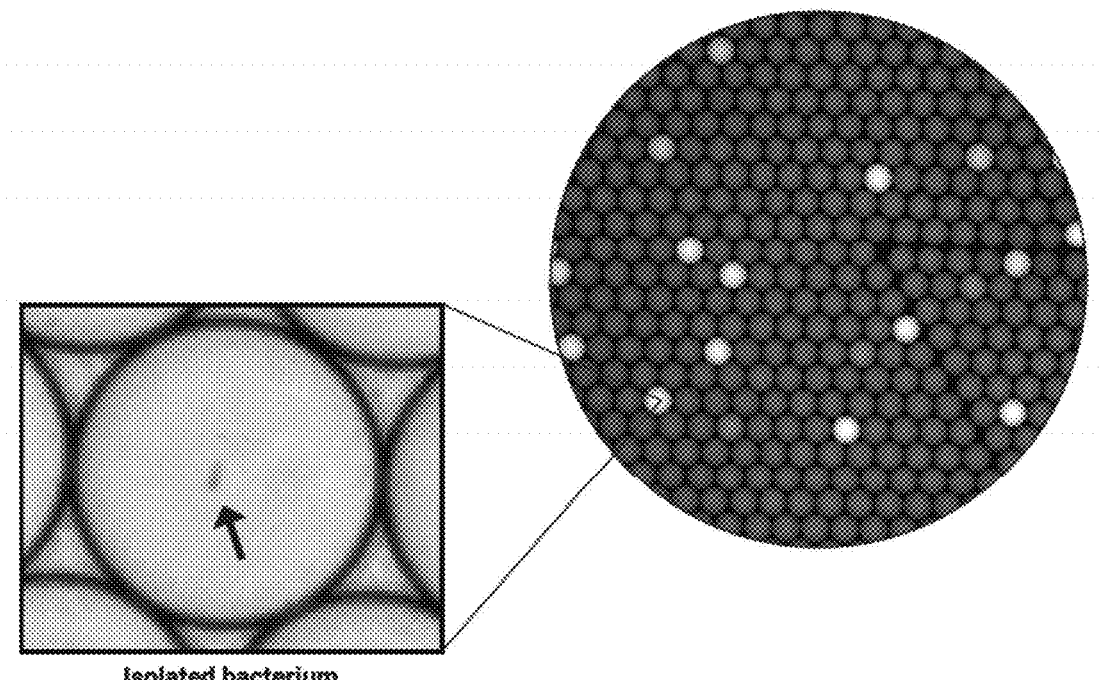
FIG. 16 shows the visualization of an isolated bacterium in a droplet monolayer.
Figure 17:
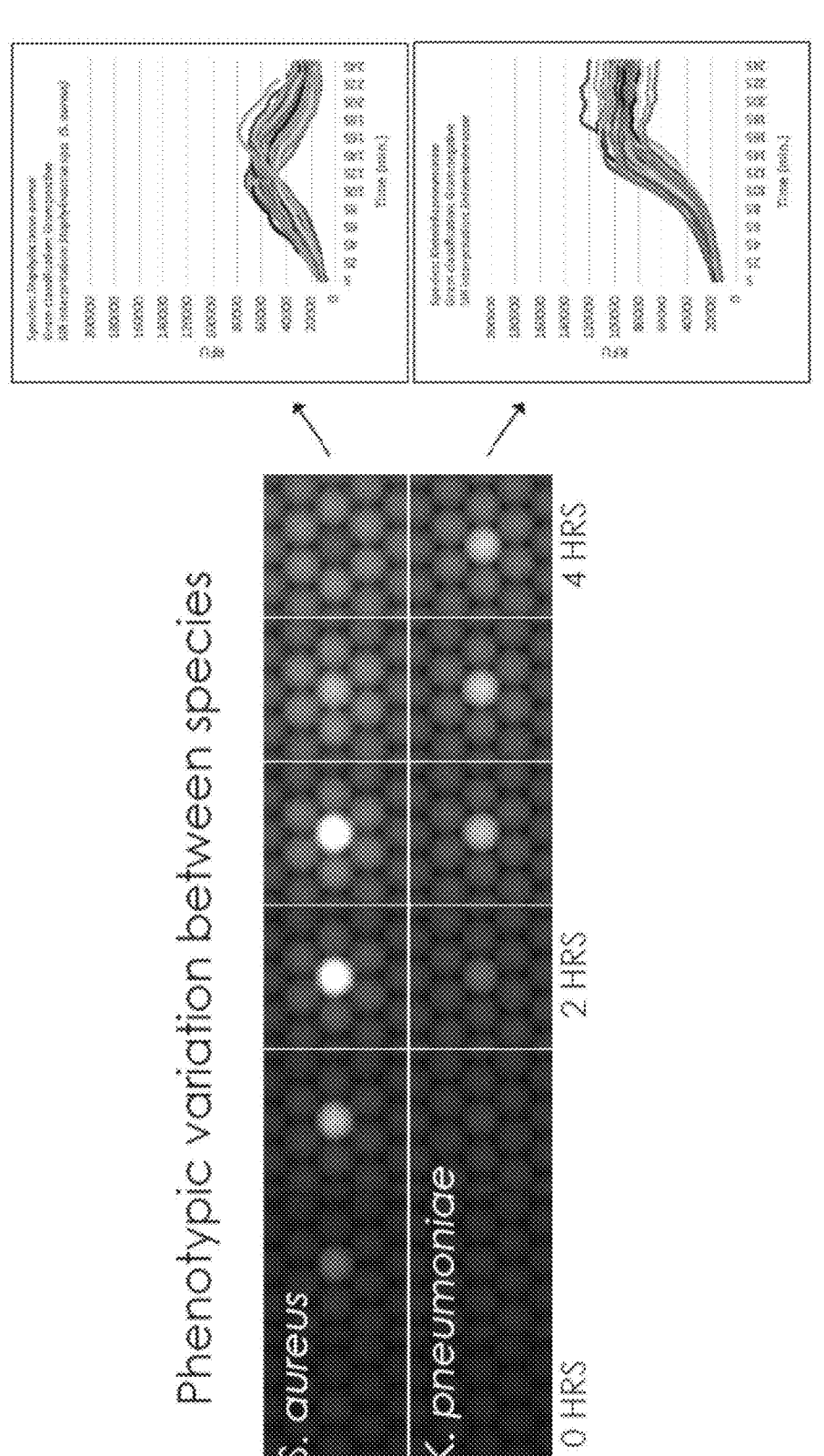
FIG. 17 illustrates distinct waveform characteristic between S. aureus and K. pneumoniae with multiple waveforms from a droplet array. The waveforms are clearly distinguishable.
Figure 19:
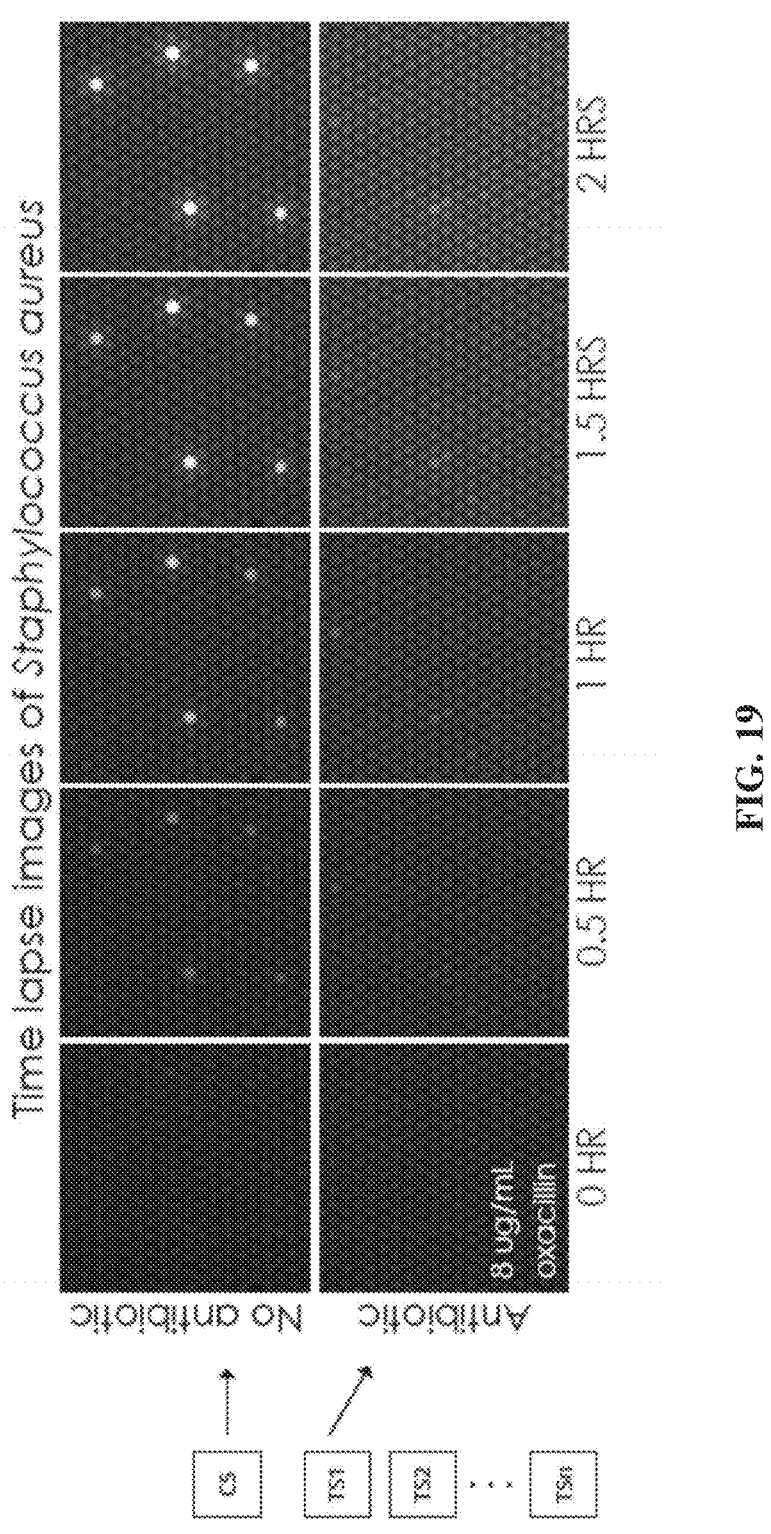
FIG. 19 shows time lapse images of S. aureus from 0 to 2 hours with and without antibiotic.

Patient Prognoses. In addition to patient diagnoses, the methods as generally described in FIG. 9 can be optimized to provide patient prognostic information, such as patient morbidity, mortality, and hospital length of stay. FIG. 11 provides a schematic of the waveform signal chain. Both the control and test partition waveforms are fed into the same N1, CH, and CL but the resulting statistics are fed into separate input nodes of a predictor neural network (N2), allowing for a detailed comparison of the variation present in CS and TS. FIG. 12 illustrates one example of using this general scheme to provide a prognosis by testing or evaluating multiple drugs. In other aspects the methods can include various other sources of information, such as imaging data, biomarker, patient information, community information, and the like (e.g., see FIG. 13).

One advantage of the methods described herein is that a diagnosis can be optimized using machine learning using sample partition statistics combined with other laboratory results, patient information, and community information to arrive at the most accurate and comprehensive diagnosis and prognosis in addition to those described in FIG. 10, including but not limited to:

Recommended Antimicrobial Drug. An antibiogram can provide clinicians with a set of antibiotics that will likely be effective against the microorganism causing the infection. It is still up to the clinician, however, to select the preferred antibiotic. An advantage of the methods described herein is that a diagnostic test can be optimized to improved patient outcomes based on the phenotypic cell profile of the infection combined with relevant patient information, community information, imaging data, and disease markers. In a certain embodiment the diagnostic test can be optimized to the final clinical decision that needs to be taken: which drug to administer and at which dose.

Patient information includes any information in the patient's health record and current condition, including but not limited to primary or secondary diagnoses, age, previous treatment history, and/or underlying conditions. Patient information can also include biometric data derived from a wearable or recorded in a personal application software.

Community information is the aggregate medical information related to a patient community, including, but not limited to genetic information; age; nationality; ethnicity; residence; place of work; socio-economic group; behavioral habit; lifestyle habit; environmental conditions; chemical exposure; pollutant and the like. If the patient has a microbial infection, community surveillance and hospital antibiogram information may play a big role in distinguishing between a between set of antimicrobial candidates. In certain aspects the patient community can be limited to a group of patients at risk of, or currently or previously having a disease, condition or combination thereof; a geographical region such as a neighborhood, city, county, state, country, continent, etc.; a demographic community having one or more common demographic; or the like.

Disease markers include any information that is relevant to the condition being tested that is derived from other laboratory tests including cytokines, microRNA, antibodies, cell-free DNA, human genomic information, blood chemistries etc., that can be used in combination with phenotypic cell data to improve diagnosis.

Imaging data includes patient sonogram, X-rays, CAT scan, PET scan, MRI, and the like. This type of data is typically interpreted by a clinician. In certain aspects raw imaging data can be encoded using a neural network to create a sparse representation and fed into the predictor neural net, e.g., N1, to aid in diagnosis.

The cell profile obtained from the methods described herein combined with patient history of antibiotic treatment could be used to predict the risk of a patient developing an antimicrobial resistant infection in the future, i.e., identifying a resistance risk. It can also be used, in combination with community information to predict outbreak risk.

I. Machine Learning and Deep Learning

Data scientists leverage machine learning techniques to build models that make predictions from real data. Typically, there are several pre-processing steps applied to raw data before machine learning models are applied to the data. Some examples of pre-processing steps include data quality processes (e.g., imputations and outlier removal), and feature extraction processes. Traditionally, such processes and models are built to work with either big data samples ("big data") (e.g., a large number of data samples, for example terabytes or more of data that are too large to fit on a single machine and thus must be stored across multiple machines) or small data samples ("small data") (e.g., a small number of data samples, for example kilobytes or megabytes of data that can be easily stored and processed on a single machine). Training sets are provided to a machine learning unit, such as a neural network or a support vector machine. Using the training set, the machine learning unit may generate a model to classify the sample according to components based on waveforms.

Artificial neural networks (NNets) mimic networks of "neurons" based on the neural structure of the brain. They process records one at a time, or in a batch mode, and "learn" by comparing their classification of the record (which, at the outset, is largely arbitrary) with the known actual classification of the record. In multilayer perceptron neural nets (MLP-NNets), the errors from the initial classification of the first record are fed back into the network and are used to modify the network's algorithm the second time around, and so on for many iterations.

In certain embodiments a fluorogenic response, or other signal, is measured over time and all measurement are collected into a set of waveforms. In certain aspects the waveforms can be clustered into known classes based on characteristic features using a neural network previously trained to recognize components in a sample. Certain aspects take a population of individual responses and use machine learning to extract clinically relevant information useful for diagnosis, treatment, and community health assessment and monitoring.

For example, providers have treated symptomatic patients with antibiotics while waiting for the culture results. This can lead to ineffective treatment, mistreatment, or over treatment of antibiotic which can have adverse consequences on both the individual patient and the population at large. Because aspects of this invention can be used to evaluate antimicrobial susceptibility that can be completed in 2 to 6 hours, effective treatment can begin much earlier.

Because this invention describes a machine learning technique to extract clinically relevant information from patient samples, the best models can be determined and optimized without the bias of the architect. Hidden structure in the data can be uncovered by machine learning that may not be readily apparent to human observation.

For example, methods can be used to acquire pathogenic microbial samples at various levels of antibiotic resistance of all target pathogens and target antibiotics the assay is designed to test. Segment these samples into control samples and antibiotic susceptibility samples at various known levels of resistance. Let $\lambda$ be a random variable with Poisson distribution. For each control sample, compartmentalize the sample into discrete units that contain $\lambda$ microbial pathogen mixed with a fluorogenic agent, or other reagent. For each antibiotic susceptibility sample, and for each antibiotic compartmentalize the sample into discrete units that contain $\lambda$ microbial pathogens mixed with the antibiotic and a fluorogenic agent, or other reagent. Measure the fluorogenic response, or other signal, of each compartmentalized microbe over time and collect all signals into a set of waveforms. Partition the signals into two classes positive and negative waveforms based on an optical metric that effectively determines which compartments are populated with non-zero pathogens (positives) and which are empty (negatives).

Particular embodiments compartmentalize bacterial cells and resazurin dye inside oil droplets suspended in an aqueous emulsion. In this embodiment $\lambda<1$ is determined based on the dynamic range requirements of the assay. Droplets are loaded into an imaging chamber and a sequence of images are taken over a period of 2-6 hours. Droplets are identified in each image and are correlated over the sequence of images by software to produce waveforms of the mitochondrial resazurin/resorufin reduction. The software then segments the waveforms into "positives" and "negatives" using OTSU segmentation, kernel density estimation, or fixed threshold segmentation after applying an optical metric on each waveform. Additionally, the preferred embodiment filters any merged droplets, stacked droplets, and uncorrelated droplets.

After gathering waveform data, the data is partitioned into two set for cross validation: a training set and a test set. Each positive waveform is normalized so that it has N points in the time dimension and its fluorescence dimension ranges from 0.0 to 1.0.

Training begins with an unsupervised learning step to reduce the dimension of each waveform from N points to a smaller number M=4 to 10. By normalizing in the fluorescence (or signal) dimension the relative magnitude of the curves are ignored and the shape of the curves become important. An auto-encoder is trained to reduce the dimensionality from N to a small number M=4 to 10. The training data is further segmented into a subset for training the auto-encoder and a subset for testing the auto-encoder. In the preferred embodiment the auto-encoder is a neural network with a 1-D convolutional layer followed by a fully connected layer of size M. An activation function such as tanh is applied that puts the range of the output on 0.0 to 1.0. The output of these M activations becomes the "encoding" for each waveform in M dimensions. Other methods to reduce the dimensionality of the data exist such as principal component analysis and eigenvector decomposition exist and may be useful as well.

Next the optimal number of waveform "classes" K is determined. In the preferred embodiment, the optimal value K is determined by iteratively applying "K means clustering" with various values of K. For each K, the distortion of the fit is computed, and the best value is chosen based on statistical methods such as the "elbow method" or rate distortion methods such as the "jump method" or "broken line method". After the optimal value K is determined, the curves are classified according to nearest neighbor classification among the K cluster centers. This completes the unsupervised training step.

Training continues with a supervised step that models a regression function $F_{(t,d)}=\mu$ mapping a target antibiotic and a digest of waveforms to an antibiotic susceptibility metric. In the preferred embodiment the antibiotic susceptibility metric is the antibiotic minimum inhibitory concentration, and a digest of waveforms is a vector of $4(K+1)$ elements as follows: the concatenation of the following:

(1) A vector of $K+1$ elements where each element $0<=j<k$ is the ratio of waveform class "j" occurring among the positive droplets in the control sample, and where the element at $j=k$ is the ratio of the negatives occurring in the control sample.

(2) A vector of $K+1$ elements where elements are similarly defined as (1) except are the ratio of the average intensity of each class of droplet waveforms vs the average intensity of all droplet waveforms in the control sample.

(3) A vector of $K+1$ elements where elements are similarly defined as (1) except from the antibiotic susceptibility test sample.

(4) A vector of $K+1$ elements where elements are similarly defined as (2) except from the antibiotic susceptibility test sample.

In the preferred embodiment the model is a deep neural network with $4(K+1)$ input nodes, a number of hidden layers, and one output node corresponding to the antibiotic susceptibility metric. In an alternative embodiment the antibiotic susceptibility metric is a unit-less value ranging from 0 to 1 where 0 denotes no antibiotic resistance and 1 denotes complete antibiotic resistance defined as no difference from the control. After the regression function is trained, the function is evaluated for accuracy by using the data withheld for the test data set.

In the preferred embodiment the training data is augmented by:

(1) Constructing waveform digests on a random sampling of waveforms in each datum.

(2) Using M-nearest neighbor classification when classifying each positive waveform before constructing the waveform digests. For each positive waveform w, find the set M closest waveform cluster centers to w among all K. The vector v of $K+1$ elements $j=0$ to $K+1$ is a weighted average such that the at position j in M is the amount of proximity w is to each center j, and that at position j not in M is 0. Examples of an "amount of proximity" could be an inverse distance weighting or evaluated from a probability distribution.

(3) A perturbation of the waveform digests by a random variable with small variance followed by a re-normalization.

When performing an antibiotic susceptibility test on a patient sample, the sample is loaded into $A+1$ circuits where circuit number A contains no antibiotic and is the control data, and each circuit number $j=0$ to $A-1$ contains a specific antibiotic j and is the antibiotic j's susceptibility data. The microbes are compartmentalized, the fluorogenic response (or other signal) is measured over time, and waveforms are extracted and segmented into "positives" and "negatives" as previously described. For each circuit j normalize and classify the waveforms. For each circuit $j=0$ to $A-1$, construct a digest d(j) as previously described containing the waveforms from circuits j and A. Evaluate the regression function $F_{(j,d(j))}$ to determine the antibiotic susceptibility metric. Map this antibiotic susceptibility metric to a clinical result such as an SIR value or a MIC value based on a standard curve or table defined by the training data.

In certain aspects the Characterizer can receive a variety of inputs and send a variety of outputs depending on the goal of the analysis being performed. In certain examples of inputs and outputs into the Characterizer: outputs—(i) Average max signal of all the waveforms in a partition, (ii) Area under the curve for all the waveforms in a partition; (iii) Average max derivative for all the waveforms in a partition; (iv) Average point in time when each waveform cross a particular threshold value for all the waveforms in a partition; (v) Same as above except using "median" instead of "average"; (vi) Same as above except for using normalized waveforms, where each waveform is divided by the average signal at the same time-point of the waveforms in a negative compartments (compartments without cells) within the same partition. Examples of inputs into the Classifier include (i) Raw waveforms and/or (ii) Dimensionally reduced waveforms, in addition to the above inputs with patient information, community information, and/or imaging data.

Furthermore, by using the auto-encoder to perform some unsupervised learning on the positive waveforms (the waveforms that actually show growth), the inventors can derive clusters of data in the encoded vector space. The number of clusters might be more than the number of bacterial species if the distribution of some species is multi-modal in the encoded vector space. Call the number of clusters K and label them 1 through K inclusive. For each negative waveform (waveform that did not show growth) in the control partition, count it as belonging to cluster 0. For each positive waveform in the control partition, determine the cluster that it most likely belongs to.

Additional inputs into the characterizer include (i) A vector of K+1 elements j=0 to K where element j corresponds to the average of the max fluorescence values of all waveforms belonging to cluster j; (ii) A vector of K+1 elements j=0 to K where element j corresponds to the average area under the waveform fluorescence curve of all waveforms belonging to cluster j; (iii) A vector of K+1 elements j=0 to K where element j corresponds to the average of the max derivative fluorescence values of all waveforms belonging to cluster j; (iv) A vector of K+1 elements j=0 to K where element j corresponds to the average point in time each waveform fluorescence curve first attains a particular threshold value among all waveforms belonging to cluster j; (v) Similarly defined for "median" instead of "average"; (vi) Same as above except for using normalized waveforms, where each waveform is divided by the average signal at the same time-point of the waveforms in cluster 0 (compartments without cells) as well as others.

II. General Methods

In certain aspects, the processing of a sample does not require lysis or washing. Since intact cells are used, only whole cells need to be manipulated rather than nucleic acid molecules, which are much more difficult manipulate due to their small size and propensity for charge-based interactions with different materials. Furthermore, the cells can be incubated at a single temperature, typically a relatively low temperature in the range of 25 to 45° C., obviating the need for thermal cycling equipment required for most NATs, which reduces cost and workflow complexity of the currently described invention. Advantageously, by avoiding high temperature steps, the invention avoids significant issues that can arise with fluid evaporation and/or bubbles that can disrupt the integrity of the reaction and/or the fluorescent readout.

A test sample or a portion of a sample comprising at least one target cell can be compartmentalized, with or without being combined with a reagent, e.g., a viability dye or reporter, into compartments or droplets such that a statisti-cally significant number of compartments or droplets contain no more than one cell or aggregation of cells (some cells tend to aggregate into cell clusters or chains). A reagent can be acted upon to produce or not produce a signal in the presence of a cell. Each droplet is monitored over time and the data used to identify and characterize each compartment. Further details on the processes of the invention are provided below.

Sample. Cells in the sample can include bacteria, fungi, plant cells, animal cells, or cells from any other cellular organism. The cells may be cultured cells or cells obtained directly from naturally occurring sources. The cells may be obtained directly from an organism or from a biological sample obtained from an organism, e.g., from sputum, saliva, urine, blood, cerebrospinal fluid, seminal fluid, stool, and tissue. In one embodiment the sample includes cells that are isolated from a biological sample comprising a variety of other components, such as other cells (background cells), viruses, proteins, and cell-free nucleic acids. The cells may be infected with a virus or another intracellular pathogen. The isolated cells may then be re-suspended in different media than those from which they were obtained. In one embodiment the sample comprises cells suspended in a nutrient medium that enables them to replicate and/or remain viable. The nutrient media may be defined media with known quantities or all ingredients or an undefined media where the nutrients are complex ingredients such yeast extract or casein hydrolysate, which contain a mixture of many chemical species of unknown proportions, including a carbon source such as glucose, water, various salts, amino acids and nitrogen. In one embodiment, the target cells in the test sample comprise pathogens and the nutrient media comprises a commonly used nutrient broth (liquid media) for culturing pathogens such as lysogeny broth, Mueller-Hinton broth, nutrient broth or tryptic soy broth. In any embodiment the media may be supplemented with a blood serum or synthetic serum to facilitate the growth of fastidious organisms.

Compartmentalization. Certain methods of the invention involve combining a sample or sample portion comprising a cell or a portion of the sample with one or more reagents and/or one or more reactants then compartmentalizing the sample or sample portion. The sample is compartmentalized such that a statistically significant portion of the compartments contain no more than one target cell or cell aggregate. The number of compartments can vary from hundreds to millions depending on the application. Compartment volumes can also vary between 1 μL to 100 nL depending on the application, but preferably between 25-500 μL. The methods described herein are compatible with any compartmentalization method.

One non-limiting method of compartmentalization is the use of droplets. While the methods for droplet formation differ, all the methods disperse an aqueous phase, the test sample in this case, into an immiscible phase, also referred to as the continuous phase, so that each droplet is surrounded by an immiscible carrier fluid. In one embodiment the immiscible phase is an oil. In certain aspects, the oil can comprise a surfactant. In a related embodiment, the immiscible phase is a fluorocarbon oil comprising a fluorosurfactant. An important advantage to using a fluorocarbon oil is that it is able to dissolve gases relatively well and it is biologically inert. Thus, the fluorocarbon oil used in the methods described herein comprises solubilized gases necessary for cell viability.

One non-limiting example of droplet formation is by using Laplace pressure gradients (see, for example, Dangla et al., 2013, *PNAS* 110(3):853-58). Laplace pressure is the differential pressure between the inside and outside of a curved surface, such as the difference in pressure between the inside and outside of a droplet. An aqueous phase containing cells or microbes can be introduced into a device having a reservoir of a continuous phase (i.e., immiscible fluid) forming an aqueous "tongue" in an appropriate device. The device can incorporate height variation(s) into a micro-channel that subject the immiscible interfaces to a difference in curvature between the portion of the aqueous phase that has not encountered the height variation and the portion of the aqueous phase downstream of the height variation. As the aqueous phase flows through the height variation, a critical curvature is reached for the portion of the aqueous phase downstream of the height variation beyond which the two portions cannot remain in static equilibrium, breaking of the aqueous phase into a droplet, as the downstream portion detaches from the tongue formed by introduction of the aqueous phase into a continuous phase, the size of the drops being determined by the device geometry. The height varia-tion can be accomplished with a single step change in the height of a microchannel (step emulsification), multiple steps (multi-step emulsification), and a ramp or similarly gradual gradients of confinement.

Reporters. A variety of reporters may be used as a reagent with the systems and methods disclosed herein. For example, a reporter can be a fluorophore, a protein labeled fluorophore, a protein comprising a photo oxidizable cofac-tor, a protein comprising another intercalated fluorophore, a mitochondrial vital stain or dye, a redox reactive dye, a membrane localizing dye, a dye with energy transfer prop-erties, a pH indicating dye and/or any molecule that is composed of a dye and a moiety that can be acted upon by an enzyme. In a further aspect the reporter can be or include a resazurin dye, acridine, a tetrazolium dye, coumarin dye, an anthraquinone dye, a cyanine dye, an azo dye, a xanthene dye, an arylmethine dye, a pyrene derivative dye, a ruthe-nium bipyridyl complex dye or derivatives thereof. Cell viability dyes, which are also included in the term reporter used herein, are used as analysis reagents to identify and characterize individual cells or pathogens encapsulated within droplets. Viability dyes have been used since the 1950's for cell viability purposes. However, these reagents are typically employed in samples that are significantly greater than 1 microliter in volume and/or are used as an endpoint assay to indicate the presence of viable cells. Aspects of the invention use a viability dye in droplets that are between 1 μL and 100 nL, and more specifically 25-500 pL. In the method described here the optical signal generated by the viability dye is concentrated by the small droplet volume and measured and recorded over an incubation time. In droplets containing viable cells, this results in an optical signature that is rapidly generated and has information about the characteristics of the cell encapsulated within the drop-lets. Combined with an environment stressor, such as an antimicrobial or cytotoxic drug, an additional signature can be generated by monitoring the optical signal of the droplets containing a cell over time. The optical signatures from the cell with and without the environmental stressor can be used to determine the identity and/or characteristics of the cell. Furthermore, the differences between the optical signatures obtained from a species of cells exposed to a drug compared to the optical signatures for same species of target cells that are not exposed to the drug can be used to determine the phenotypic drug resistance profile for the target cells obtained from a test sample. Because these signatures are generated from individual cells encapsulated in droplets, they represent information about the individual characteris-tics of each cell as opposed to an average characteristic of a population of cells that is generated from a bulk sample containing many cells.

The methods described herein are compatible with any viability dye or reporter or fluorogenic or luminogenic enzyme substrate that can be used with live cells (does not require cell lysis). In a preferred embodiment the viability dye is a resorufin-based dye or derivative thereof. An example is resazurin which, when it is irreversibly reduced to pink and highly fluorescent resorufin (FIG. 6) it produces a fluorescent signal and a colorimetric shift (from blue to pink). In a preferred embodiment, the fluorescence is used because it offers better sensitivity over colorimetric signal changes. The limited-diffusion confinement within a sub-nanoliter volume of secreted fluorescent molecules quickly concentrates to detectable signal levels and is then detected by the methods described below. Furthermore, resorufin is reversibly reduced to non-fluorescent hydroresorufin (FIG. 6) if the redox environment dips below a particular redox threshold, usually around −100 mV. The combination of irreversible reduction from resazurin to resorufin and the reversible reduction of resorufin to hydroresorufin and oxi-dation of hydroresorufin back to resorufin depending on the redox potential of the droplet are what create the unique fluorescence signature over time in droplets that are small enough volume such that redox changes occur quickly in the presence of a single cell or cell aggregate. Examples of commercially available resazurin-based dyes are: Alamar-Blue™ (various), PrestoBlue™ (Thermo Fisher Scientific), Cell-titer Blue™ (Promega), or Resazurin sodium salt pow-der (Sigma-Aldrich). Dyes that are structurally related to resazurin and can be also be used in the method are: 10-acetyl-3, 7-dihydroxyphenoxazine (also known as Amplex Red™), C12 resazurin, and 1,3-dichloro-7-hy-droxy-9,9-dimethylacridine-2(9H)-one (DDAO dye). In alternate embodiments, resorufin is modified with a cleav-able moiety that acts as a fluorogenic substrate. Examples of commercially available resorufin-based fluorogenic sub-strates are 7-ethoxyresorufin, resorufin-β-D-glucoronic acid, resorufin-β-glucoronic-acid methyl ester. In alternate embodiments dyes that rely on tetrazolium-reduction, such as formazan dyes, can be used as the cell viability indicator. Examples include INT, MTT, XTT, MTS, TTC or tetrazo-lium chloride, NBT, and the WST series. In alternate embodiments, the reporter can include fluorogenic sub-strates such as 4-methylumbelliferone (4-MU), ethyl 7-hy-droxycoumarin-3-carboxylate (EHC), 7-amido-4-methyl-coumarin (AMC), fluorescein, and resorufin. In alternate embodiments, the reporter can be an Aldol® indicator (Biosynth). In alternate embodiments, the reporter can include luminogenic substrates such as luminol, Shaap deoxetanes, luciferin derivatives and proto-substrates, and dioxetane derivatives. Chemiluminescent reporters can be combined with fluorescent reporters to increase cell-specific waveform variation that aids in distinguishing similar DCCs. In certain aspects the reporter is a dioxetane deriva-tive that carries a specific enzyme labile group. When exposed to an enzyme expressed by the isolated cell, the enzyme labile group is cleaved, liberating the corresponding unstable phenolate anion which decomposes, generating a high energy intermediate which emits light by returning to its unexcited ground state. An example of a dioxetane derivative is AquaSpark (Biosynth). Luciferase proto-sub-strates can also be combined with fluorescent and/or chemi-luminescent reporters to increase cell-specific variation. The proto-substrate is reduced into a luciferase substrate within the isolated cell and then subsequently oxidized by a luciferase to produce a bioluminescent signal. Examples include Real-time Glo (Promega).

The invention provides for multiplexing of non-luminogenic, e.g., fluorescent, colorimetric, and/or luminogenic assays. As used herein, a "luminogenic assay" includes a reaction in which a molecule once acted on by a cellular component is luminogenic. Luminogenic assays include chemiluminescent and bioluminescent assays including but not limited to those which employ or detect luciferase, β-galactosidase, β-glucuronidase, β-lactamase, a protease, alkaline phosphatase, or peroxidase, and suitable corresponding substrates, e.g., modified forms of luciferin, coelenterazine, luminol, peptides or polypeptides, dioxetanes, dioxetanones, and related acridinium esters. As used herein, a "luminogenic assay reagent" includes a substrate, as well as an activator or enzyme that cleaves or modifies the substrate for a luminogenic reaction.

In certain aspects one or more isolated cell can harbor or express an enzyme useful in producing a luminogenic reaction. In particular, enzymes that are useful in the present invention include any protein that exhibits enzymatic activity, e.g., lipases, phospholipases, sulphatases, ureases, arylamidases, peptidases, proteases, oxidases, catalases, nitrate reductases, and esterases, including acid phosphatases, glucosidases, glucuronidases, galactosidases, carboxylesterases, and luciferases. In one embodiment, one of the enzymes is a hydrolytic enzyme. In another embodiment, at least two of the enzymes are hydrolytic enzymes. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, and β-D-glucosiduronase.

For alkaline phosphatase, it is preferable that the substrate includes a phosphate-containing dioxetane, such as 3-(2'-spiroadamantane)-4-methoxy-4-(3"-phosphoryloxy)phenyl-1,2-dioxetane, disodium salt, or disodium 3-(4-methoxyspiro[1,2-dioxetane-3,2'(5'-chloro)-tricyclo-[3.3.1.1$^{3,7}$] decan]-4-yl)phenyl phosphate, or disodium 2-chloro-5-(4-methoxyspiro{1,2-dioxetane-3,2'-(5'-chloro)-tricyclo {3.3.1.13,7]decan}-4-yl)-1-phenyl phosphate or disodium 2-chloro-5-($^4$-methoxyspiro{1,2-dioxetane-3,2'-tricyclo [3.3.1.13,7]decan}-4-yl)-1-phenzyl phosphate (AMPPD, CSPD, CDP-Star® and ADP-Star™, respectively).

For β-galactosidase, the substrate preferably includes a dioxetane containing galactosidase-cleavable or galactopyranoside groups. The luminescence in the assay results from the enzymatic cleavage of the sugar moiety from the dioxetane substrate. Examples of such substrates include 3-(2'-spiroadamantane)-4-methoxy-4-(3"-β-D-galactopyranosyl) phenyl-1,2-dioxetane (AMPGD), 3-(4-methoxyspiro[1,2-dioxetane-3,2'-(5'-chloro)tricyclo[3.3.1.1$^{3,7}$]-decan]-4-yl-phenyl-β-D-galactopyranoside (Galacton®), 5-chloro-3-(methoxyspiro[1,2-dioxetane-3,2'-(5'-chloro)tricyclo [3.3.1$^{3,7}$]decan-4-yl-phenyl-β-D-galactopyranoside (Galacton-Plus®), and 2-chloro-5-(4-methoxyspiro[1,2-dioxetane-3,2'(5'-chloro)-tricyclo-[3.3.1.1$^{3,7}$]decan]-4-yl)phenyl β-D-galactopyranoside (Galacton-Star®).

In assays for β-glucuronidase and β-glucosidase, the substrate includes a dioxetane containing β-glucuronidase-cleavable groups such as a glucuronide, e.g., sodium 3-(4-methoxyspiro     {1,2-dioxetane-3,2'-(5'-chloro)-tricyclo [3.3.1.1$^{3,7}$]decan}-4-yl)phenyl-β-D-glucuronate (Glucuron™). In assays for a carboxyl esterase, the substrate includes a suitable ester group bound to the dioxetane. In assays for proteases and phospholipases, the substrate includes a suitable enzyme-cleavable group bound to the dioxetane.

Preferably, the substrates for each enzyme in the assay are different. For assays which include one dioxetane containing substrate, the substrate optionally contains a substituted or unsubstituted adamantyl group, a Y group which may be substituted or unsubstituted and an enzyme cleavable group. Examples of preferred dioxetanes include those mentioned above, e.g., those referred to as Galacton®, Galacton-Plus®, CDP-Star®, Glucuron™, AMPPD, Galacton-Star®, and ADP-Star™, as well as 3-(4-methoxyspiro{1,2-dioxetane-3,2'-(5'-chloro)-tricyclo[3.3.1.1$^{3,7}$]decan}-4-yl)phenyl-β-D-glucopyranoside (Glucon™), CSPD, disodium 3-chloro-5-(4-methoxyspiro{1,2-dioxetane-3,2'(5'-chloro)-tricyclo-[3.3.1.1$^{3,7}$]decan)-4-yl)-1-phenyl phosphate (CDP).

Cell (DCC) Aggregates. A preferred application of the invention is towards the diagnosis of microbial infections by identifying the microbes causing the infection and whether or not they are resistant to antimicrobial drugs. Thus, in this application, the DCCs can be single-celled microbes. Some bacteria, however, aggregate naturally into clusters or chains. In these cases, some droplets may comprise an aggregate of cells of the same microbial species (homogenous aggregate) rather than a single microbe. In these cases, the shape of the curve may be affected by the number of cells in the aggregate. However, the stored signature waveforms and call logic that are used to classify the compartmentalized cells can account for such aggregates the same way they can account for single cells. Furthermore, if the embodiment includes antimicrobial susceptibility testing the mixture comprising the antimicrobial drug will exhibit the same cell aggregation characteristics as the mixture that excludes the antimicrobial drug and the comparison will still be accurate. Therefore, while the method of the invention generally comprises isolation of single cells in each droplet, it necessarily accommodates the case of a single cell species in a homogenous aggregate isolated in the droplet rather individual cells. In the case of cancer disease diagnosis, the target DCCs typically do not aggregate if they are circulating tumor cells. If the cancer cells are obtained from tissue, the tissue is typically disintegrated into individual cells prior to analysis. Therefore, each droplet will contain at most one cell; however, in some instances a cancer aggregate may also be analyzed using the described methods.

Signal Detection. Once the droplets have been generated, they must be presented for analysis by an optical system, sensor, or sensor array. In a preferred embodiment, the droplets are presented in a two-dimensional array so that good thermal control can be maintained, and the droplet signals can be measured simultaneously (at a single instance in time) for many droplets. In the droplets containing target cells, the reporter will produce a concentrated fluorescent signal that will rise above the background droplets that do not contain cells. The concentrated signal of the droplet enables single cell identification in comparable time standard PCR techniques which are the gold standard for fast identification. In certain aspects the signal is detected by exciting a reduced reporter with a specific wavelength of light and collecting the bandpass-filtered, Stokes-shifted light with a camera. The advantage to use imaging techniques is that they can image a droplet array that remains stationary and can therefore easily be monitored over time. Cytometry based methods typically employ endpoint detection instead of real time detection because of the difficulty in keeping track of the moving droplets over time. Another advantage to imaging the array is that all the droplets experience the same reaction conditions at the time of analysis. Therefore, droplet signals can be compared at equivalent time points which is important since signals vary over time. With a cytometry approach, droplets pass by the detector at different times. Therefore, some droplets are incubated longer than others at the time of analysis. Finally, there may be different target cell species in the test sample. For each species, there may be an optimal droplet volume and dye or reporter concentration that maximizes signal at a particular time point. If an endpoint method is used, droplet volume and reporter concentrations do not need be controlled to the same degree because time can compensate for sub optimality and different species can be characterized universally within a single dye and droplet concentration.

Multiplexing. The methods described herein include the specific identification of multiple cells from a single test sample. By compartmentalizing single cells into their own isolated droplet, competition for resources between cells is eliminated. Therefore, individual cells that would exist collectively as a minority in a bulk population, now have equal access to nutrients when compared to the majority population of cells which results in a higher sensitivity for low abundance cells in a sample with multiple cells types. The multiplexing limitations for this invention depend on the ability to differentiate viability signatures between different cell types. Most methods for multiplexing require multiple dyes (fluorophores) which, in turn, require multiple sets of LEDs, excitation, and emission filters. Because the method described herein uses shape information rather than spectral information, the method can be used to multiplex many targets with a single dye or reporter requiring only one LED, emission filter, and excitation filter, thus simplifying the hardware needed to perform the analysis. In other embodiments, multiple reporters could be used in combination, together or separately, wherein reporters are selected from a set of different spectral wavelengths or luminogenic classes (e.g., fluorescence, chemiluminescence or colorimetric) such that multiple orthogonal metabolic pathways could be measured for each droplet of interest. For example, a redox sensitive fluorogenic dye such as resazurin could be used in combination with a second fluorogenic reporter for enzyme activity, such as fluorescein beta-galactopyranoside and a bioluminescent reporter such as luciferin/luciferase. Any number of additional reporters could be used in combination where each reporter would provide unique bacteria specific information.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Core Technology

Individual microbial cells are encapsulated into pico-scale droplets with a cell viability dye that becomes fluorescent in the presence of a live cell. In certain embodiments a resazurin-based dye is used. In the presence of a live cell, resorufin molecules will rapidly concentrate within the picoscale droplet environment and produce an easily detectable fluorescent signal.

The rate at which each microbe reduces resazurin depends on cell-specific characteristics such as permeability, metabolic profile, size, and growth rate. Furthermore, within the pico-scale environment inside the droplet, the encapsulated microbe will dominate the conditions (e.g., redox potential) that determine whether resorufin will reduce to hydroresorufin. The result is that different microbial species produce unique fluorescent "signatures" over time allowing us to identify the microbes in each droplet.

Additional fluorogenic reagents may also be incorporated into these assays as needed to increase signal variation and thereby add specificity to the signatures as needed. Moreover, antimicrobial susceptibility (AST) can be measured by introducing an antimicrobial drug into the droplets and comparing the viability signals from those droplets that contain an antimicrobial drug to those that do not contain an antimicrobial drug.

The reactions are observed in real-time by arranging tens-of-thousands of droplets into a two-dimensional array and recording the fluorescence from each droplet using a wide-field imaging system with LED excitation and CMOS sensor detection.

Neural net powered by deep learning. Machine learning can be used to recognize microbes by their fluorescent signatures and to determine drug susceptibility. Specifically, a proprietary deep neural network architecture can be used to interpret identification (ID) and antibiotic susceptibility (AST) results. By leveraging machine learning, bacteria can be classified based on phenotypic differences apparent at single-cell resolution, allowing seamless integration of pathogen identification and antibiotic susceptibility using the same detection modality. This discovery uniquely allows reduced test costs and complexity. The neural net input data is based on time-series images from a two-dimensional droplet array. The proprietary software identifies and tracks the droplets over time and generates a per-droplet waveform of fluorescence intensity with respect to time.

For the purposes of bacterial ID, only 'control' circuits with no antibiotic are used. Each droplet is classified and total droplets for each species are counted. For each antibiotic, a control circuit where no antibiotic is present, is compared to the test circuit where an antibiotic is present at a specified concentration. The neural network will determine the effectiveness of the antibiotic by comparing how the waveforms change between the control and antibiotic test circuits.

Pathogen Identification. Taken together, ID and AST provide clinicians with the definitive information required to precisely treat a bacterial infection. The value of pathogen identification depends on when AST results become available. Under the current paradigm, ID results are available hours, sometimes days before AST results are available. Without timely AST results, there is an increased burden on ID to provide speciation in order to help clinicians adjust the antibiotic regimen.

For example, in the absence of an AST result, a clinician will want to distinguish between *Acinetobacter baumannii* and other *Acinetobacter* species because *A. baumannii* is often resistant to certain antibiotics that the other Acinetobacters are not.

However, if the AST results are available at the same time as the ID results there is no need to distinguish between *A. baumannii* and other Acinetobacters because the full resistance profile is revealed and, according to the CLSI guidelines, the actions guided by AST results are identical for all *Acinetobacter* species.

When ID and AST results are available simultaneously, the ID result is used to interpret the AST result according to CLSI guidelines, producing an antibiogram for the infection (an antibiogram is a list of the antibiotics that were tested and whether the infection is susceptible (S), intermediate (I), or resistant (R) to each listed antibiotic. This is widely considered the most clinically important test result in the microbiology laboratory.

A. Results

Sensitivity and specificity statistics are depicted in Table 1 (TP stands for True Positives, TN for True Negatives, FP for False Positives, and FN for False Negatives). Table 2 details the discordant results.

Antibiotic Susceptibility Testing. Most AST platforms require multiple concentrations of the same antibiotic to observe a differential bacterial response correlating to antibiotic efficacy. Broth microdilution, for example, requires seven dilutions of each antibiotic. The Vitek2 requires at least three concentrations per antibiotic. The plan is to include up to 25 antimicrobials per test which is not possible unless one can test most of the antibiotics at a single concentration.

Just as with ID, the investigators have an enormous amount of qualitative data supporting the ability to do AST, but unlike ID, until now, quantitative evidence was lacking for moving forward with development. The AST neural net architecture is more complicated and requires far more data for supervised learning than the ID neural net. Therefore, in order to generate AST data, the system had to be far enough along to generate an order of magnitude more droplet data per day than when ID feasibility data was collected.

TABLE 1

| | | | | | | Sensitivity and specificity | |
|---|---|---|---|---|---|---|---|
| | Strains | TP | FN | TN | FP | Sensitivity | Specificity |
| Species | | | | | | | |
| *S. aureus* | 3 | 35 | 1 | 115 | 2 | 97.2% (85.8-99.5) | 98.3% (94-99.5) |
| *E. faecium* | 3 | 9 | 0 | 144 | 0 | 100.0% (70.1-100) | 100.0% (97.4-100) |
| Enterobacteriaceae | 7 | 102 | 2 | 49 | 0 | 98.1% (93.3-99.5) | 100.0% (92.7-100) |
| *P. aeruginosa* | 2 | 4 | 0 | 148 | 1 | 100.0% (51-100) | 99.3% (96.3-99.9) |
| | 15 | 150 | 3 | 456 | 3 | 98.0% (94.4-99.3) | 99.3% (98.1-99.8) |
| Enterobacteriaceae | | | | | | | |
| *K. pneumoniae* | 5 | 86 | 8 | 59 | 0 | 91.5% (84.1-95.6) | 100.0% (93.9-100) |
| *E. coli* | 2 | 10 | 0 | 137 | 6 | 100.0% (72.2-100) | 95.8% (91.1-98.1) |

35

TABLE 2

| | | | | | | Discordant Results | |
|---|---|---|---|---|---|---|---|
| | Strains | TP | FN | TN | FP | Sensitivity | Specificity |
| Species | | | | | | | |
| *S. aureus* | 3 | 10711 | 1260 | 39102 | 1657 | 89.5% | 95.9% |
| *E. faecium* | 3 | 1759 | 92 | 50256 | 623 | 95.0% | 98.8% |
| Enterobacteriaceae | 7 | 36622 | 2175 | 13560 | 373 | 94.4% | 97.3% |
| *P. aeruginosa* | 2 | 103 | 8 | 51737 | 882 | 92.8% | 98.3% |
| | 15 | 49195 | 3535 | 154655 | 3535 | 93.3% | 97.8% |
| Enterobacteriaceae | | | | | | | |
| *K. pneumoniae* | 5 | 28978 | 6651 | 16406 | 695 | 81.3% | 95.9% |
| *E. coli* | 2 | 2791 | 377 | 45031 | 4531 | 88.1% | 90.9% |

The results presented in Table 2 are on a per droplet basis (i.e., each positive droplet was viewed as an independent culture isolate). This method more effectively stresses the neural network because population statistics cannot be leveraged in the call, biasing performance estimates towards more stringency.

This study included many of the most important pathogens according to prevalence and mortality. Importantly, the study included phylogenetically similar species: two pathogens from the Enterobacteriaceae family that the investigators were able to discriminate under identical conditions. These results were all collected in Difco LB Broth (Becton Dickinson 244620).

In this study, Categorical Agreement (CA) is measured as referenced against broth microdilution preformed according to CLSI procedure. For example, 100% categorical agreement means that each time the reference called a pathogen as "susceptible" or "resistant", the test did the same. This is the most clinically relevant result in ID/AST testing and will be heavily scrutinized during FDA clearance.

As mentioned, this is the first quantitative evaluation of our AST method against broth microdilution (the gold standard). As this is an ongoing evaluation, it is too soon to make any firm conclusions. However, thus far, the results are encouraging.

US 12,595,505 B2

TABLE 3

AST Results by antibiotic

| | CA | CI (95%) | Agreement | Total Tested | Error Type |
|---|---|---|---|---|---|
| Amikacin (10/10) | 100.0% | (72.2-100.0) | 10 | 10 | |
| Aztreonam (11/13) | 84.6% | (57.8-95.7) | 11 | 13 | VME (2) |
| Cefoxitin (11/11) | 100.0% | (74.1-100.0) | 11 | 11 | |
| Ceftriaxone (22/23) | 95.7% | (79.0-99.2) | 22 | 23 | ME |
| Ciprofloxacin (22/22) | 100.0% | (85.1-100.0) | 22 | 22 | |
| Erythromycin (10/10) | 100.0% | (72.2-100.0) | 10 | 10 | |
| Gentamicin (26/26) | 100.0% | (87.1-100.0) | 26 | 26 | |
| Levofloxacin (20/20) | 100.0% | (83.9-100.0) | 20 | 20 | |
| Meropenem (16/16) | 100.0% | (80.6-100.0) | 16 | 16 | |
| Tobramycin (19/19) | 100.0% | (83.2-100.0) | 19 | 19 | |
| Vancomycin (24/25) | 96.0% | (80.5-99.3) | 24 | 25 | ME |
| Totals | 97.9% | (94.8-99.2) | 191 | 195 | |

VME—very major error; R called S
ME—major error, S called R

TABLE 4

AST results by pathogen

| Bacteria | Antibiotic | % CA | CI | | Susceptible | Resistant | Isolates (S) | Isolates (R) | Total Strains |
|---|---|---|---|---|---|---|---|---|---|
| *S. aureus* | Cefoxitin | 100.0% | (74.1-100.0) | (11/11) | 5 | 6 | 1 | 1 | 3 total |
| (4 hrs) | Ciprofloxacin | 100.0% | (51.0-100.0) | (4/4) | 1 | 3 | 1 | 1 | strains |
| | Erythromycin | 100.0% | (72.2-100.0) | (10/10) | 5 | 5 | 1 | 1 | |
| | Gentamicin | 100.0% | (72.2-100.0) | (10/10) | 5 | 5 | 1 | 1 | |
| | Vancomycin | 100.0% | (79.6-100.0) | (15/15) | 11 | 4 | 2 | 1 | |
| *E. faecium* | Ciprofloxacin | 100.0% | (34.2-100.0) | (2/2) | 1 | 1 | 1 | 1 | 3 total |
| (4 hrs) | Vanomycin | 90.0% | (59.6-98.2) | (9/10) | 5 | 5 | 2 | 1 | strains |
| *K. pneumoniae* | Amikacin | 100.0% | (34.2-100.0) | (2/2) | 1 | 1 | 1 | 1 | 4 total |
| (4 hrs) | Aztreonam | 84.6% | (57.8-95.7) | (11/13) | 6 | 7 | 1 | 2 | strains |
| | Ceftriaxone | 95.7% | (79.0-99.2) | (22/23) | 5 | 18 | 1 | 2 | |
| | Ciprofloxacin | 100.0% | (64.6-100.0) | (7/7) | 6 | 1 | 1 | 1 | |
| | Gentamicin | 100.0% | (56.6-100.0) | (5/5) | 5 | 0 | 1 | 0 | |
| | Levofloxacin | 100.0% | (56.6-100.0) | (5/5) | 4 | 1 | 2 | 1 | |
| | Meropenem | 100.0% | (72.2-100.0) | (10/10) | 2 | 8 | 1 | 2 | |
| | Tobramycin | 100.0% | (64.6-100.0) | (7/7) | 3 | 4 | 1 | 2 | |
| *E. coli* | Ciprofloxacin | 100.0% | (43.8-100.0) | (3/3) | 1 | 2 | 1 | 1 | 2 total |
| (4 hrs) | Tobramycin | 100.0% | (43.8-100.0) | (3/3) | 1 | 2 | 1 | 1 | strains |
| *P. aeruginosa* | Amikacin | 100.0% | (67.6-100.0) | (8/8) | 4 | 4 | 2 | 1 | 4 total |
| (4 hrs) | Ciprofloxacin | 100.0% | 61.0-100.0) | (6/6) | 2 | 4 | 1 | 1 | strains |
| | Gentamicin | 100.0% | (74.1-100.0) | (11/11) | 7 | 4 | 2 | 1 | |
| | Levofloxacin | 100.0% | (79.6-100.0) | (15/15) | 7 | 8 | 2 | 1 | |
| | Meropenem | 100.0% | (61.0-100.0) | (6/6) | 5 | 1 | 3 | 1 | |
| | Tobramycin | 100.0% | (70.1-100.0) | (9/9) | 5 | 4 | 2 | 1 | |
| | | 97.9% | (94.8-99.2) | (191/195) | 97 | 98 | 32 | 26 | |

B. Materials and Methods

Pathogen identification. Multiple subcultures of *Pseudomonas aeruginosa* (ATCC 15442), *Klebsiella pneumoniae* (ATCC 33495), and *Staphylococcus aureus* (ATCC BAA-977) were incubated overnight at 37° C. in Trypticase Soy Broth (Becton Dickinson 211825); strains of *Acinetobacter baumannii* (ATCC 19606), *Escherichia coli* (ATCC 25922), and *Staphylococcus epidermidis* (ATCC 14990) were incubated at 37° C. overnight in Difco Nutrient Broth (Becton Dickinson 234000); and *Enterococcus faecium* strain ATCC 19434 was incubated overnight at 37° C. in Brain Heart Infusion (Sigma 53286-100G).

Contrived samples were prepared by seeding Difco LB Broth (Becton Dickinson 244620) from the overnight subcultures with 10% resazurin-based dye. Dilutions were prepared and tested in order to achieve a Poisson distribution of the individual cells or individual cell clusters (monoclonal) within the droplet partitions. The samples were partitioned using step-emulsification into approximately 30,000 pico-liter volume droplets (195 pico-liters). The droplets were arranged into a monolayer and imaged using a Leica DMI 6000B fluorescence microscope. Images were captured at 5-minute intervals. Each droplet was tracked across time using our proprietary image processing software which generates a "waveform" (fluorescent intensity over time) for each droplet. In this experiment, shape-based features were then extracted from each waveform so that the investigators could minimize neural net optimization time and maximize training performance over a small data set.

Antibiotic susceptibility testing. Strains were obtained from isolate collections at ATCC, BEI, and the CDC. Strain identities were confirmed using published biochemical methods. Antibiotics were prepared and validated according CLSI procedures. Antimicrobial susceptibility reference results of the isolates were determined by broth microdilution using cation-adjusted Mueller-Hinton broth according to published CLSI procedures.

Contrived samples were prepared by seeding broth with colonies from subculture plates including 10% resazurin-based dye. Each sample was then split wherein each microfluidic chip contained one no-antibiotic control and up to 7 different antibiotics. Up to 4 chips, were loaded into our prototype instrument wherein each circuit of a given chip simultaneously generated a droplet array, which was incubated and imaged over the course of 4 hours. The resultant images were processed into waveforms and AST calls were generated by pair-wise analysis of control and unique antibiotic.

The preceding description and examples, as well as the figures are included to demonstrate particular aspects of the invention. It should be appreciated by those of skill in the art that the techniques disclosed in the description, examples, or figures represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

What is claimed:

1. A method for evaluating a sample, the method comprising:
   (a) dividing the sample into two or more sub-samples or sample portions;
   (b) mixing each sub-sample or sample portion with one or more reagents and/or one or more reactants forming distinct sub-sample or sample portion mixtures;
   (c) compartmentalizing each of the sub-sample or sample portion mixtures into a plurality of droplets having an average volume of less than 1 µL, wherein some of the droplets contain one cell or one cellular aggregate;
   (d) detecting signals over time from some of the droplets;
   (e) collecting the detected signals to provide collected droplet data;
   (f) generating a classifier output for the one cell or one cellular aggregate at least by transmitting the collected droplet data to at least a first neural network; and
   (g) generating an analysis output with a second neural network at least by transmitting the classifier output to a second neural network.

2. The method of claim 1, wherein the sample is an environmental sample or a biological sample.

3. The method of claim 1, wherein the sample is a biological sample that is a sample from a patient.

4. The method of claim 3, wherein the patient is a human patient.

5. The method of claim 3, wherein the biological sample is bronchoalveolar lavage (BAL), sputum, saliva, urine, blood, cerebrospinal fluid, seminal fluid, stool, swab, scraping, pus, or tissue.

6. The method of claim 1, wherein:
   the sub-samples or sample portions include a control sub-sample or sample portion and at least one test sub-sample or sample portion;
   the control sub-sample or sample portion is not mixed with a reactant; and
   each test sub-sample or sample portion is mixed with a reactant.

7. The method of claim 6, wherein each of the sub-samples or sample portions is mixed with a reagent that is a reporter or a signal generating moiety.

8. The method of claim 1, wherein at least one of the sub-samples or sample portions is mixed with a reactant that is a nutrient mix or a drug.

9. The method of claim 1, wherein at least one of the sub-samples or sample portions is mixed with a reagent that is a fluorogenic or luminogenic reagent.

10. The method of claim 1, wherein generating the classifier output further comprises:
   generating a neural network output from the first neural network, wherein the first neural network comprises an autoencoder configured to reduce a dimensionality of the collected droplet data such that a dimensionality of the neural network output is less than a dimensionality of the collected droplet data; and
   transmitting the neural network output to a classifier to generate the classifier output.

11. The method of claim 10, further comprising:
   transmitting the collected droplet data to a characterizer to generate a characterizer output; and
   wherein generating the analysis output with the second neural network comprises transmitting the characterizer output to the second neural network.

12. The method of claim 11, wherein the analysis output is a determination of a clinical endpoint.

13. The method of claim 12, wherein the clinical endpoint is a patient outcome, a minimum inhibitory concentration of a drug, a susceptible or resistant cell, or a prognosis.

14. The method of claim 13, wherein:
   the clinical endpoint is a prognosis; and
   the prognosis is a length of hospital stay or subject risk of adverse event.

15. The method of claim 12, wherein:
   the sub-samples or sample portions include at least one test sub-sample or sample portion that is mixed with a reactant that is an antimicrobial drug;
   some of the droplets each contain a microbe; and
   the clinical endpoint is a minimum inhibitory concentration of the antimicrobial drug or a susceptible or resistant cell.

16. The method of claim 15, wherein the sub-samples or sample portions include a control sub-sample or sample portion that is not mixed with an antimicrobial drug.

17. The method of claim 16, wherein each of the sub-samples or sample portions is mixed with a reagent that is a fluorogenic or luminogenic reagent.

18. The method of claim 16, wherein:
   the neural network output includes:
      a control neural network output generated by the first neural network from collected droplet data for the control sub-sample or sample portion;
      a test neural network output generated by the first neural network from collected droplet data for the at least one of the sub-samples or sample portions that is mixed with the reactant;
   the classifier output includes:
      a control classifier output generated by the classifier from the control neural network output; and
      a test classifier output generated by the classifier from the test neural network output;
   the characterizer output includes:
      a control characterizer output generated by the characterizer from the collected droplet data for the control sub-sample or sample portion; and
      a test characterizer output generated by the characterizer from the collected droplet data for the at least one of the sub-samples or sample portions that is mixed with the reactant; and the second neural network includes a plurality of input nodes, wherein transmitting the classifier output and the characterizer output to the second neural network is performed such that:

the control classifier and characterizer outputs are transmitted to a first set of the input nodes of the second neural network; and the test classifier and characterizer outputs are transmitted to a second set of the input nodes of the second neural network that are different than the first set.

19. The method of claim 11, wherein generating the analysis output further comprises transmitting community information and patient information to the second neural network.

\* \* \* \* \*